US012746368B2

(12) United States Patent
Howell

(10) Patent No.: US 12,746,368 B2

(45) Date of Patent: Sep. 29, 2026

(54) RAPIDLY INSERTABLE CENTRAL CATHETERS, CATHETER INSERTION ASSEMBLIES, AND METHODS

(71) Applicant: Bard Access Systems, Inc., Salt Lake City, UT (US)

(72) Inventor: Glade H. Howell, Draper, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 620 days.

(21) Appl. No.: 17/746,113

(22) Filed: May 17, 2022

(65) Prior Publication Data

US 2022/0362524 A1 Nov. 17, 2022

Related U.S. Application Data

(60) Provisional application No. 63/189,549, filed on May 17, 2021.

(51) Int. Cl.

*A61M 25/06* (2006.01)
*A61M 25/00* (2006.01)
*A61M 25/09* (2006.01)

(52) U.S. Cl.

CPC .... *A61M 25/0668* (2013.01); *A61M 25/0026* (2013.01); *A61M 25/0052* (2013.01);
(Continued)

(58) Field of Classification Search

CPC ............ A61M 5/3293; A61M 25/0668; A61M 25/0904; A61M 25/0141; A61M 25/0054;
(Continued)

(56) References Cited

U.S. PATENT DOCUMENTS 3,076,457 A 2/1963 Simon
3,359,978 A 12/1967 Smith, Jr.
(Continued)

FOREIGN PATENT DOCUMENTS

CN 106422031 B 7/2021
CN 114870208 A 8/2022
(Continued)

OTHER PUBLICATIONS

PCT/US2022/039742 filed Aug. 8, 2022 International Preliminary Report on Patentability dated Feb. 13, 2024.
(Continued)

*Primary Examiner* — Matthew F Desanto
(74) *Attorney, Agent, or Firm* — Rutan & Tucker LLP

(57) ABSTRACT

Rapidly insertable central catheters (“RICCs”), RICC insertion assemblies, and methods are disclosed. For example, a RICC insertion assembly can include a RICC, an introducer, and an access guidewire. An introducer needle can include a needle shaft having a longitudinal gap extending from a proximal portion of the needle shaft through a needle tip. An introducer sheath can include a splittable sheath hub coupled to a splittable sheath body. The introducer sheath can be disposed over the introducer needle with the sheath body sealing the needle shaft for drawing a vacuum through the introducer needle. The access guidewire can extend along an entirety of a primary lumen of the RICC, through a splittable valved port of the sheath hub, along a sheath body-covered needle channel of the needle shaft, and to a location in the introducer proximal of the needle tip in a ready-to-operate state of the RICC insertion assembly.

11 Claims, 11 Drawing Sheets

(52) U.S. Cl.
CPC .... *A61M 25/0097* (2013.01); *A61M 25/0606* (2013.01); *A61M 25/0905* (2013.01)

(58) Field of Classification Search
CPC ............ A61M 25/0052; A61M 25/065; A61M 25/0606; A61M 2025/0004; A61M 2025/0006; A61M 2025/0183; A61M 2025/0059; A61M 2025/0681; A61M 2025/09191; A61M 2039/0258; A61M 2025/0675; A61M 2025/0034
See application file for complete search history.

(56) References Cited

U.S. PATENT DOCUMENTS

| | | | |
|---|---|---|---|
| 3,539,034 A | 11/1970 | Tafeen | |
| 4,411,654 A | 10/1983 | Boarini et al. | |
| 4,743,265 A | 5/1988 | Whitehouse et al. | |
| 4,886,507 A | 12/1989 | Patton et al. | |
| 4,935,008 A | 6/1990 | Lewis, Jr. | |
| 4,957,489 A | 9/1990 | Cameron et al. | |
| 4,988,356 A | 1/1991 | Crittenden et al. | |
| 4,994,040 A | 2/1991 | Cameron et al. | |
| 5,255,690 A | 10/1993 | Keith et al. | |
| 5,261,887 A | 11/1993 | Walker | |
| 5,290,244 A | 3/1994 | Moonka | |
| 5,380,290 A | 1/1995 | Makower et al. | |
| 5,687,727 A | 11/1997 | Kraus et al. | |
| 5,735,813 A | 4/1998 | Lewis | |
| 5,836,306 A | 11/1998 | Duane et al. | |
| 5,853,391 A | 12/1998 | Bell | |
| 5,971,957 A | 10/1999 | Luther et al. | |
| 6,019,736 A * | 2/2000 | Avellanet | A61M 25/09 604/103.1 |
| 6,159,195 A | 12/2000 | Ha et al. | |
| 7,172,587 B2 | 2/2007 | Poole et al. | |
| 7,938,820 B2 | 5/2011 | Webster et al. | |
| 8,882,713 B1 | 11/2014 | Call et al. | |
| 11,819,638 B2 | 11/2023 | Howell et al. | |
| 11,918,767 B2 | 3/2024 | Howell et al. | |
| 12,161,820 B2 | 12/2024 | Howell et al. | |
| 2002/0004635 A1 | 1/2002 | Yock | |
| 2002/0072712 A1 | 6/2002 | Nool et al. | |
| 2003/0205843 A1 | 11/2003 | Adams | |
| 2004/0092879 A1 | 5/2004 | Kraus et al. | |
| 2004/0236346 A1 * | 11/2004 | Parker | A61M 25/005 604/524 |
| 2005/0021124 A1 | 1/2005 | Cunniffe et al. | |
| 2005/0043684 A1 * | 2/2005 | Basta | A61M 25/09041 604/167.03 |
| 2005/0251092 A1 | 11/2005 | Howell et al. | |
| 2006/0129091 A1 | 6/2006 | Bonnette et al. | |
| 2007/0100294 A1 | 5/2007 | Sugita et al. | |
| 2007/0276288 A1 | 11/2007 | Khaw | |
| 2008/0009793 A1 | 1/2008 | Dabbs | |
| 2008/0027380 A1 | 1/2008 | Wholey et al. | |
| 2008/0091137 A1 | 4/2008 | Reavill | |
| 2008/0262430 A1 | 10/2008 | Anderson et al. | |
| 2009/0187147 A1 | 7/2009 | Kurth et al. | |
| 2011/0071502 A1 | 3/2011 | Asai | |
| 2013/0184659 A1 | 7/2013 | Byrnes et al. | |
| 2014/0100552 A1 | 4/2014 | Gallacher et al. | |
| 2015/0119806 A1 | 4/2015 | Blanchard et al. | |
| 2015/0224287 A1 | 8/2015 | Bian et al. | |
| 2015/0314109 A1 | 11/2015 | Minar et al. | |
| 2015/0320968 A1 * | 11/2015 | Konstantino | A61M 29/02 606/194 |
| 2016/0175563 A1 | 6/2016 | Woehr et al. | |
| 2016/0220786 A1 | 8/2016 | Mitchell et al. | |
| 2016/0310704 A1 | 10/2016 | Ng et al. | |
| 2017/0035996 A1 | 2/2017 | O'Fallon | |
| 2017/0258489 A1 | 9/2017 | Galili et al. | |
| 2017/0296792 A1 | 10/2017 | Ornelas Vargas et al. | |
| 2018/0043138 A1 | 2/2018 | Chu | |
| 2019/0015637 A1 | 1/2019 | Jacobs | |
| 2019/0022353 A1 | 1/2019 | Khanicheh et al. | |
| 2019/0022359 A1 | 1/2019 | Khanicheh et al. | |
| 2019/0038113 A1 | 2/2019 | Chu | |
| 2019/0134374 A1 | 5/2019 | Korkuch et al. | |
| 2020/0008838 A1 | 1/2020 | Frey et al. | |
| 2020/0107859 A1 | 4/2020 | Zhu | |
| 2020/0147349 A1 | 5/2020 | Holt | |
| 2020/0170559 A1 | 6/2020 | Burkholz et al. | |
| 2020/0188650 A1 | 6/2020 | Al-Ali | |
| 2020/0197682 A1 | 6/2020 | Franklin et al. | |
| 2021/0085927 A1 | 3/2021 | Howell | |
| 2021/0121661 A1 | 4/2021 | Howell | |
| 2021/0330941 A1 | 10/2021 | Howell et al. | |
| 2021/0332274 A1 | 10/2021 | Hoshi et al. | |
| 2021/0361915 A1 | 11/2021 | Howell et al. | |
| 2021/0402153 A1 | 12/2021 | Howell et al. | |
| 2022/0168548 A1 | 6/2022 | Dong | |
| 2022/0370762 A1 | 11/2022 | Blanchard et al. | |
| 2023/0039733 A1 | 2/2023 | Howell | |
| 2023/0041261 A1 | 2/2023 | Howell | |
| 2023/0043989 A1 | 2/2023 | Howell | |
| 2023/0064542 A1 | 3/2023 | Howell | |
| 2023/0086639 A1 | 3/2023 | Howell | |
| 2023/0096377 A1 | 3/2023 | West et al. | |
| 2023/0149667 A1 | 5/2023 | Lindekugel et al. | |
| 2023/0181878 A1 | 6/2023 | Blanchard et al. | |
| 2023/0201537 A1 | 6/2023 | Howell et al. | |
| 2023/0201538 A1 | 6/2023 | Howell et al. | |
| 2023/0218867 A1 | 7/2023 | Howell et al. | |
| 2023/0381481 A1 * | 11/2023 | Pizzato | A61M 39/0247 |
| 2024/0082549 A1 | 3/2024 | Spataro et al. | |
| 2024/0226507 A1 | 7/2024 | Spataro | |
| 2025/0375594 A1 | 12/2025 | Lindekugel | |
| 2026/0021276 A1 | 1/2026 | Blanchard et al. | |

FOREIGN PATENT DOCUMENTS

| | | | |
|---|---|---|---|
| DE | 4136051 | A1 | 7/1993 |
| DE | 19750090 | A1 | 6/1999 |
| EP | 0067260 | A1 | 12/1982 |
| EP | 0155331 | A1 | 9/1985 |
| EP | 0499147 | A2 | 8/1992 |
| EP | 0641571 | A1 | 3/1995 |
| EP | 1338299 | A1 | 8/2003 |
| EP | 3193813 | A1 | 7/2017 |
| EP | 3473291 | A1 | 4/2019 |
| JP | H02255156 | A | 10/1990 |
| JP | H077971 | Y2 | 3/1995 |
| JP | 2004254879 | A | 9/2004 |
| JP | 2009232917 | A | 10/2009 |
| JP | 5101359 | B2 | 12/2012 |
| JP | 2016042544 | A1 | 3/2016 |
| WO | 8906986 | A1 | 8/1989 |
| WO | 95/09662 | A1 | 4/1995 |
| WO | 98/10821 | A1 | 3/1998 |
| WO | 99/59651 | A2 | 11/1999 |
| WO | 02/078776 | A2 | 10/2002 |
| WO | 2005096778 | A2 | 10/2005 |
| WO | 2009094089 | A1 | 7/2009 |
| WO | 2011143621 | A1 | 11/2011 |
| WO | 2012101089 | A1 | 8/2012 |
| WO | 2013064215 | A1 | 5/2013 |
| WO | 2015/061172 | A1 | 4/2015 |
| WO | 2016123278 | A1 | 8/2016 |
| WO | 2016187063 | A1 | 11/2016 |
| WO | 2020206280 | A2 | 10/2020 |
| WO | 2021216902 | A1 | 10/2021 |
| WO | 2021222116 | A2 | 11/2021 |
| WO | 2022/204049 | A1 | 9/2022 |
| WO | 2022/246271 | A2 | 11/2022 |
| WO | 2022/245774 | A3 | 12/2022 |
| WO | 2023014994 | A1 | 2/2023 |
| WO | 2023018669 | A1 | 2/2023 |
| WO | 2023018729 | A1 | 2/2023 |
| WO | 2023018733 | A1 | 2/2023 |
| WO | 2023028138 | A2 | 3/2023 |
| WO | 2023049174 | A1 | 3/2023 |
| WO | 2023091586 | A1 | 5/2023 |
| WO | 2023114324 | A1 | 6/2023 |

(56) References Cited

FOREIGN PATENT DOCUMENTS

| | | | |
|---|---|---|---|
| WO | 2023122312 | A1 | 6/2023 |
| WO | 2023129457 | A1 | 7/2023 |
| WO | 2023137077 | A1 | 7/2023 |
| WO | 2024059073 | A1 | 3/2024 |
| WO | 2024151869 | A1 | 7/2024 |
| WO | 2025259604 | A1 | 12/2025 |

OTHER PUBLICATIONS

PCT/US2022/041368 filed Aug. 24, 2022 International Preliminary Report on Patentability dated Feb. 27, 2024.
PCT/US2022/044242 filed Sep. 21, 2022 International Preliminary Report on Patentability dated Mar. 26, 2024.
PCT/US2022/053887 filed Dec. 22, 2022 International Search Report and Written Opinion dated May 8, 2023.
PCT/US2022/021187 filed Mar. 21, 2022 International Search Report and Written Opinion dated Jun. 17, 2022.
PCT/US2022/052884 filed Dec. 14, 2022 International Search Report and Written Opinion dated May 15, 2023.
PCT/US2022/053724 filed Dec. 21, 2022 International Search Report and Written Opinion dated May 10, 2023.
PCT/US2023/010623 filed Jan. 11, 2023, International Search Report and Written Opinion dated Jul. 6, 2023.
PCT/US2022/030365 filed May 20, 2022 International Search Report and Written Opinion dated Apr. 4, 2023.
PCT/US2022/041368 filed Aug. 24, 2022 International Search Report and Written Opinion dated Mar. 21, 2023.
PCT/US2022/044242 filed Sep. 21, 2022 International Search Report and Written Opinion dated Feb. 8, 2023.
PCT/US2022/050280 filed Nov. 17, 2022 International Search Report and Written Opinion dated Apr. 17, 2023.
PCT/US2023/032545 filed Sep. 12, 2023 International Search Report and Written Opinion dated Feb. 13, 2024.
U.S. Appl. No. 17/700,152, filed Mar. 21, 2022 Restriction Requirement dated Jan. 31, 2025.
PCT/US2022/029561 filed May 17, 2022 International Search Report and Written Opinion dated Nov. 9, 2022.
PCT/US2022/039742 filed Aug. 8, 2022 International Search Report and Written Opinion dated Dec. 21, 2022.
PCT/US2022/039852 filed Aug. 9, 2022 International Search Report and Written Opinion dated Dec. 6, 2022.
PCT/US2022/039861 filed Aug. 9, 2022, International Search Report and Written Opinion dated Jan. 5, 2023.
Adam et al. (Gastrointestinal Endoscopy vol. 77, No. 5S 2013, 1020) (Year: 2010).
Lapalu et al. "Totally implantable port management: impact of positive pressure during needle withdrawal on catheter tip occlusion (an experimental study)" The Journal of Vascular Access 2010; 11: 46-51, 2010 Wichtig Editore, Original Article, 2010.
PCT/US2024/011269 filed Jan. 11, 2024 International Search Report and Written Opinion dated May 15, 2024.
U.S. Appl. No. 17/700,152, filed Mar. 21, 2022 Non-Final Office Action dated Aug. 14, 2025.
U.S. Appl. No. 17/750,097, filed May 20, 2022 Notice of Allowance dated Jun. 27, 2025.
U.S. Appl. No. 17/883,490, filed Aug. 8, 2022 Non-Final Office Action dated Jul. 31, 2025.
U.S. Appl. No. 17/884,402, filed Aug. 9, 2022 Notice of Allowance dated Sep. 10, 2025.
U.S. Appl. No. 17/894,759, filed Aug. 24, 2022 Final Office Action dated Sep. 24, 2025.
U.S. Appl. No. 17/949,734, filed Sep. 21, 2022 Non-Final Office Action dated Aug. 4, 2025.
U.S. Appl. No. 17/989,325, filed Nov. 17, 2022 Restriction Requirement dated Aug. 28, 2025.
U.S. Appl. No. 18/081,491, filed Dec. 14, 2022 Non-Final Office Action dated Aug. 22, 2025.
PCT/US2025/032881 filed Jun. 9, 2025 International Search Report and Written Opinion dated Sep. 24, 2025.
U.S. Appl. No. 17/884,307, filed Aug. 9, 2022 Final Office Action dated Oct. 23, 2025.
U.S. Appl. No. 17/894,759, filed Aug. 24, 2022 Notice of Allowance dated Dec. 16, 2025.
U.S. Appl. No. 18/086,517, filed Dec. 21, 2022 Non-Final Office Action dated Oct. 31, 2025.
U.S. Appl. No. 18/087,676, filed Dec. 22, 2022 Restriction Requirement dated Oct. 8, 2025.
U.S. Appl. No. 18/095,968, filed Jan. 11, 2023 Restriction Requirement dated Nov. 24, 2025.
U.S. Appl. No. 17/700,152, filed Mar. 21, 2022 Restriction Requirement dated Apr. 29, 2025.
U.S. Appl. No. 17/750,097, filed May 20, 2022 Restriction Requirement dated Mar. 20, 2025.
U.S. Appl. No. 17/884,307, filed Aug. 9, 2022 Non-Final Office Action dated Apr. 2, 2025.
U.S. Appl. No. 17/884,402, filed Aug. 9, 2022 Non-Final Office Action dated May 30, 2025.
U.S. Appl. No. 17/894,759, filed Aug. 24, 2022 Non-Final Office Action dated Jun. 16, 2025.
U.S. Appl. No. 17/700,152, filed Mar. 21, 2022 Final Office Action dated Feb. 12, 2026.
U.S. Appl. No. 17/883,490, filed Aug. 8, 2022 Advisory Action dated Mar. 26, 2026.
U.S. Appl. No. 17/883,490, filed Aug. 8, 2022 Final Office Action dated Dec. 22, 2025.
U.S. Appl. No. 17/949,734, filed Sep. 21, 2022 Final Office Action dated Feb. 5, 2026.
U.S. Appl. No. 17/989,325, filed Nov. 17, 2022 Notice of Allowance dated Jan. 22, 2026.
U.S. Appl. No. 18/081,491, filed Dec. 14, 2022 Final Office Action dated Jan. 12, 2026.
U.S. Appl. No. 18/086,517, filed Dec. 21, 2022 Final Office Action dated Apr. 7, 2026.
U.S. Appl. No. 18/087,676, filed Dec. 22, 2022 Non-Final Office Action dated Mar. 6, 2026.
U.S. Appl. No. 18/095,968, filed Jan. 11, 2023 Non-Final Office Action dated Mar. 23, 2026.
U.S. Appl. No. 18/367,390, filed Sep. 12, 2023 Notice of Allowance dated Apr. 9, 2026.
U.S. Appl. No. 18/410,781, filed Jan. 11, 2024 Non-Final Office Action dated Mar. 25, 2026.

* cited by examiner

RAPIDLY INSERTABLE CENTRAL CATHETERS, CATHETER INSERTION ASSEMBLIES, AND METHODS

PRIORITY

This application claims the benefit of priority to U.S. Provisional Patent Application No. 63/189,549, filed May 17, 2021, which is incorporated by reference in its entirety into this application.

BACKGROUND

Central venous catheter ("CVCs") are commonly introduced into patients and advanced through their vasculatures by way of the Seldinger technique. The Seldinger technique utilizes a number of steps and medical devices (e.g., a needle, a scalpel, a guidewire, an introducer sheath, a dilator, a CVC, etc.). While the Seldinger technique is effective, the number of steps are time consuming, handling the number of medical devices is awkward, and both of the foregoing can lead to patient trauma. In addition, there is a relatively high potential for touch contamination due to the number of medical devices that need to be interchanged during the number of steps of the Seldinger technique. As such, there is a need to reduce the number of steps and medical devices involved in introducing a catheter such as a CVC into a patient and advancing the catheter through a vasculature thereof.

Disclosed herein are rapidly insertable central catheters ("RICCs"), RICC insertion assemblies, and methods that address the foregoing.

SUMMARY

Disclosed herein is a RICC insertion assembly including, in some embodiments, a RICC, an introducer, and an access guidewire disposed in both the RICC and the introducer. The introducer includes an introducer needle and a splittable introducer sheath. The introducer needle includes a needle shaft. The needle shaft includes a longitudinal gap extending from a proximal portion of the needle shaft through a needle tip. The introducer sheath includes a splittable sheath body and a splittable sheath hub coupled to a proximal portion of the sheath body. The introducer sheath is disposed over the needle shaft with the sheath body sealing the needle shaft such that a vacuum can be drawn through the introducer needle. The sheath hub includes a splittable valved port in a side of the sheath hub. The access guidewire extends along an entirety of a primary lumen of the RICC, through a valve of the port, along a sheath body-covered needle channel of the needle shaft, and to a location in the introducer proximal of the needle tip.

In some embodiments, the RICC includes a catheter tube. The catheter tube includes a first section in a distal portion of the catheter tube, a second section in the distal portion of the catheter tube proximal of the first section, and a tapered junction between the first and second sections of the catheter tube. The first section of the catheter tube is formed of a first polymeric material having a first durometer. The second section of the catheter tube is formed of a second polymeric material having a second durometer less than the first durometer. The junction has a length between that of exposed portions of the first and second sections of the catheter tube.

In some embodiments, the catheter tube possesses a column strength sufficient to prevent buckling of the catheter tube when inserted into a needle tract established by a percutaneous puncture with the introducer. The column strength of the catheter tube is also sufficient to prevent buckling of the catheter tube when advanced through a vasculature of a patient without dilation of tissue about the needle tract or any blood vessels of the vasculature beforehand with a separate dilator.

In some embodiments, the access guidewire includes a non-wound portion and a wound portion. The non-wound portion of the access guidewire extends through the valve of the port.

In some embodiments, the valve includes a tearable or split septum compressed in the port. The access guidewire extends through the septum in the RICC insertion assembly.

In some embodiments, the septum lies over a notch in the needle shaft. The longitudinal gap in the needle shaft distally extends from the notch.

In some embodiments, the sheath body is configured to split against the access guidewire when the sheath body is pulled away from the access guidewire after splitting the sheath hub.

In some embodiments, the sheath hub includes a non-tapered female sheath-hub connector in a proximal portion of the sheath hub.

In some embodiments, a needle hub coupled to a proximal portion of the needle shaft includes a non-tapered male needle-hub connector in a distal portion of the needle hub. The male needle-hub connector is configured to form a fluid-tight connection with the female sheath-hub connector.

In some embodiments, the male needle-hub connector includes an 'O'-ring disposed in a circumferential groove around the male needle-hub connector configured to form the fluid-tight connection.

In some embodiments, the RICC insertion assembly further includes a syringe. The syringe includes a tapered male syringe tip extending from a distal portion of the syringe. The syringe tip is configured to insert into a tapered female needle-hub connector in a proximal portion of the needle hub.

Also disclosed herein is an introducer for a RICC including, in some embodiments, an introducer needle and a splittable introducer sheath. The introducer needle includes a needle shaft, a needle hub coupled to a proximal portion of the needle shaft, and a needle tip in a distal portion of the needle shaft. The needle shaft includes a longitudinal gap. The longitudinal gap extends from the proximal portion of the needle shaft distal of the needle hub through the needle tip. The introducer sheath is configured to be disposed over the needle shaft in at least a ready-to-operate state of the introducer. The introducer sheath includes a splittable sheath body and a splittable sheath hub coupled to a proximal portion of the sheath body. The sheath body is configured to seal the needle shaft such that a vacuum can be drawn through the introducer needle in at least the ready-to-operate state of the introducer. The sheath hub includes a splittable valved port in a side of the sheath hub.

In some embodiments, the valve includes a tearable or split septum compressed in the port. The septum is configured to pass an access guidewire therethrough.

In some embodiments, the septum lies over a notch in the needle shaft in at least the ready-to-operate state of the introducer. The longitudinal gap in the needle shaft distally extends from the notch.

In some embodiments, the sheath hub further includes a pair of tabs radially extending from the sheath hub. The tabs are configured for splitting the sheath hub by pulling the tabs apart.

In some embodiments, the sheath hub includes a pair of longitudinal hub faults. The hub faults include a primary fault and a secondary fault. The primary fault is along a portion of a primary side of the introducer sheath including the port. The secondary fault is along a portion of a secondary side of the introducer sheath opposite the primary side. The sheath hub is configured to split along both the primary and secondary hub faults for propagation along the sheath body in the primary and secondary sides of the introducer sheath.

In some embodiments, the sheath hub includes a non-tapered female sheath-hub connector in a proximal portion of the sheath hub.

In some embodiments, the needle hub includes a non-tapered male needle-hub connector in a distal portion of the needle hub. The male needle-hub connector is configured to form a fluid-tight connection with the female sheath-hub connector in at least the ready-to-operate state of the introducer.

In some embodiments, the male needle-hub connector includes an 'O'-ring disposed in a circumferential groove around the male needle-hub connector configured to form the fluid-tight connection.

In some embodiments, a distal portion of the sheath body includes a taper tapering from an outer diameter of a majority of the sheath body down to an outer diameter of the needle shaft. The taper provides a smooth transition from the needle tip to the sheath body in the ready-to-operate state of the introducer.

In some embodiments, the taper has a taper angle less than either a tip-bevel angle of a tip bevel or a primary-bevel angle of a primary bevel of a bevel of the needle tip.

In some embodiments, the introducer further includes a syringe. The syringe includes a tapered male syringe tip extending from a distal portion of the syringe. The syringe tip is configured to insert into a tapered female needle-hub connector in a proximal portion of the needle hub.

Also disclosed herein is a RICC including, in some embodiments, a catheter tube, a catheter hub, and one or more extension legs. The catheter tube includes a first section in a distal portion of the catheter tube, a second section in the distal portion of the catheter tube proximal of the first section, and a tapered junction between the first and second sections of the catheter tube. The first section of the catheter tube is formed of a first polymeric material having a first durometer. The second section of the catheter tube is formed of a second polymeric material having a second durometer less than the first durometer. The junction has a length between that of exposed portions of the first and second sections of the catheter tube. The catheter hub is coupled to a proximal portion of the catheter tube. Each extension leg of the one-or-more extension legs is coupled to the catheter hub by a distal portion thereof.

In some embodiments, a proximal portion of the first section of the catheter tube is disposed in a bore in a distal portion of the junction and bonded thereto.

In some embodiments, a distal end of the second section of the catheter tube is flush with a proximal end of the junction and bonded thereto.

In some embodiments, the catheter tube possesses a column strength sufficient to prevent buckling of the catheter tube when inserted into a needle tract established by a percutaneous puncture. The column strength of the catheter tube is also sufficient to prevent buckling of the catheter tube when advanced through a vasculature of a patient without dilation of tissue about the needle tract or any blood vessels of the vasculature beforehand with a separate dilator.

In some embodiments, the RICC includes a set of three lumens including the primary lumen, a secondary lumen, and a tertiary lumen. The three lumens are formed of fluidly connected portions of three catheter-tube lumens, three catheter-hub lumens, and three extension-leg lumens.

In some embodiments, the primary lumen has a primary-lumen aperture in a distal end of the catheter tube. The secondary lumen has a secondary-lumen aperture in a side of the distal portion of catheter tube. The tertiary lumen has a tertiary-lumen aperture in the side of the distal portion of the catheter tube proximal of the secondary-lumen aperture.

Also disclosed herein is a method for inserting a RICC into a blood-vessel lumen of a patient. The method includes an assembly-acquiring step, a needle tract-establishing step, an access guidewire-advancing step, an introducer needle-withdrawing step, an introducer sheath-splitting step, and a RICC-advancing step. The assembly-acquiring step includes acquiring a RICC insertion assembly. The RICC insertion assembly includes the RICC, an introducer, and an access guidewire in a substantially ready-to-operate state of the RICC insertion assembly. The introducer includes an introducer needle disposed in a splittable introducer sheath fluidly connected to a syringe. The needle tract-establishing step includes establishing a needle tract from an area of skin to the blood-vessel lumen with the introducer. The access guidewire-advancing step includes advancing a distal end of the access guidewire from its initial location in the introducer proximal of a needle tip of the introducer needle into the blood-vessel lumen. The introducer needle-withdrawing step includes withdrawing the introducer needle from the introducer leaving both the introducer sheath and the access guidewire in place in the blood-vessel lumen. The introducer needle includes a longitudinal gap extending from a proximal portion of a needle shaft through the needle tip allowing the introducer needle-withdrawing step while the access guidewire remains in place in the blood-vessel lumen. The introducer sheath-splitting step includes splitting the introducer sheath away from the access guidewire to remove split portions of the introducer sheath from the blood-vessel lumen. The RICC-advancing step includes advancing a catheter tube of the RICC over the access guidewire and into the blood-vessel lumen, thereby inserting the RICC into the blood-vessel lumen.

In some embodiments, the needle tract-establishing step includes ensuring blood flashes back along the longitudinal gap of the introducer needle, into a needle hub of the introducer needle, into a syringe tip, into a barrel of the syringe, or a combination thereof, thereby confirming the needle tract extends into the blood-vessel lumen.

In some embodiments, the needle tract-establishing step includes drawing a slight vacuum with the syringe while establishing the needle tract such that the blood flashes back into introducer needle upon establishing the needle tract.

In some embodiments, the method further comprises an ultrasound-confirming step. The ultrasound-confirming step includes confirming with ultrasound imaging the access guidewire is in the blood-vessel lumen.

In some embodiments, the method further includes a blood-aspirating step. The blood-aspirating step includes aspirating blood with the syringe coupled to the introducer needle for confirmation the needle tract extends into the blood-vessel lumen before the introducer needle-withdrawing step.

In some embodiments, the sheath body seals the longitudinal gap of the needle shaft for the aspirating of the blood with the syringe.

In some embodiments, the access guidewire-advancing step secures blood-vessel access for the RICC-advancing step.

In some embodiments, the method further includes an introducer sheath-advancing step. The introducer sheath-advancing step includes advancing the introducer sheath over the introducer needle into the blood-vessel lumen before the access guidewire-advancing step. The introducer sheath-advancing step secures blood-vessel access for the RICC-advancing step.

In some embodiments, the introducer sheath-splitting step includes splitting a sheath hub including the port in the side of the sheath hub by pulling apart a pair of tabs radially extending from the sheath hub and propagating one or more splits resulting from splitting the sheath hub along a sheath body of the introducer sheath.

In some embodiments, propagating the one-or-more splits includes continuing to pull apart the tabs after splitting the sheath hub.

In some embodiments, propagating the one-or-more splits includes pulling the sheath body away from the access guidewire such that the sheath body splits against the access guidewire.

In some embodiments, the method further includes an access guidewire-withdrawing step. The access guidewire-withdrawing step includes withdrawing the access guidewire leaving the catheter tube in place in the blood-vessel lumen.

In some embodiments, the method further includes a maneuver guidewire-advancing step, an additional RICC-advancing step, and a maneuver guidewire-withdrawing step. The maneuver guidewire-advancing step includes advancing a maneuver guidewire into the blood-vessel lumen by way of a primary lumen of the RICC. The additional RICC-advancing step includes advancing a distal portion of the catheter tube farther into the blood-vessel lumen over the maneuver guidewire to a lower ⅓ of a superior vena cava ("SVC") of a heart of the patient. The maneuver guidewire-withdrawing step includes withdrawing the maneuver guidewire leaving the catheter tube in place in the lower ⅓ of the SVC.

These and other features of the concepts provided herein will become more apparent to those of skill in the art in view of the accompanying drawings and following description, which describe particular embodiments of such concepts in greater detail.

DRAWINGS

DESCRIPTION

Figure 1:
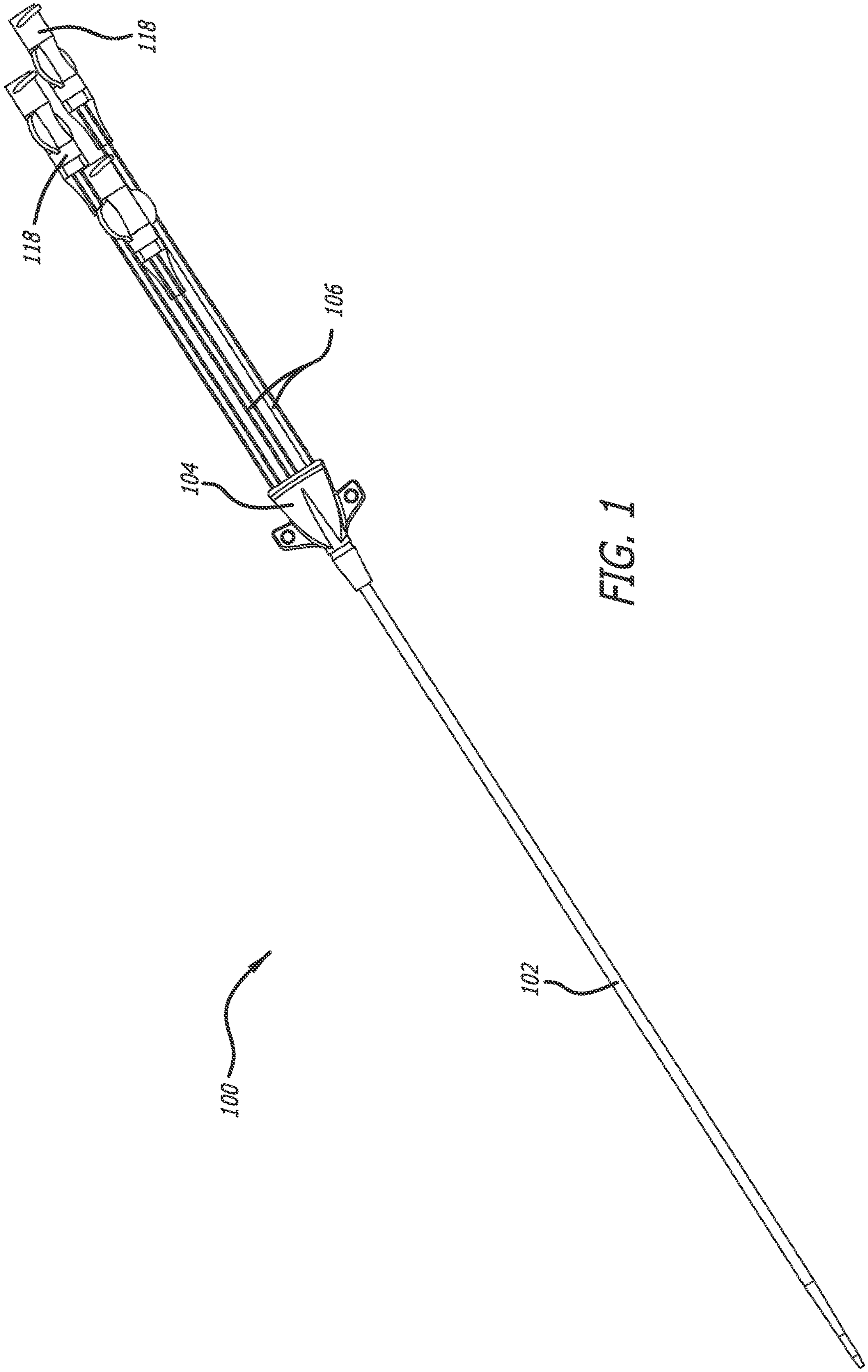
FIG. 1 illustrates a RICC in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. In addition, any of the foregoing features or steps can, in turn, further include one or more features or steps unless indicated otherwise. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a catheter includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal-end portion, or the proximal length of the catheter can include the proximal end of the catheter; however, the proximal portion, the proximal-end portion, or the proximal length of the catheter need not include the proximal end of the catheter. That is, unless context suggests otherwise, the proximal portion, the proximal-end portion, or the proximal length of the catheter is not a terminal portion or terminal length of the catheter.

With respect to "distal," a "distal portion" or a "distal-end portion" of, for example, a catheter includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal-end portion, or the distal length of the catheter can include the distal end of the catheter; however, the distal portion, the distal-end portion, or the distal length of the catheter need not include the distal end of the catheter. That is, unless context suggests otherwise, the distal portion, the distal-end portion, or the distal length of the catheter is not a terminal portion or terminal length of the catheter.

Unless defined otherwise, all technical and scientific terms used herein have the same meaning as commonly understood by those of ordinary skill in the art.

As set forth above, while the Seldinger technique is effective, the number of steps are time consuming, handling the number of medical devices is awkward, and both of the foregoing can lead to patient trauma. In addition, there is a relatively high potential for touch contamination due to the number of medical devices that need to be interchanged during the number of steps of the Seldinger technique. As such, there is a need to reduce the number of steps and medical devices involved in introducing a catheter such as a CVC into a patient and advancing the catheter through a vasculature thereof.

Disclosed herein are RICCs, RICC insertion assemblies, and methods that address the foregoing.

RICCs

Figure 2:
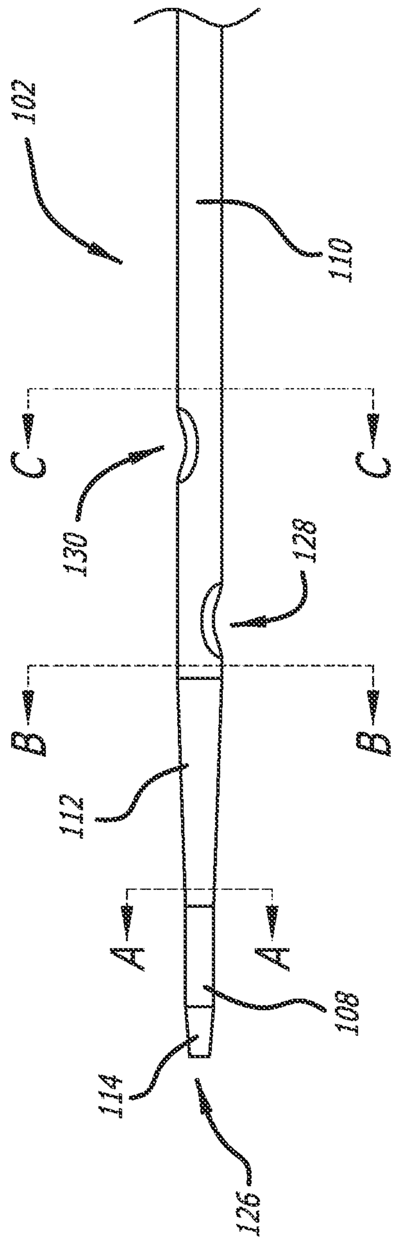
FIG. 2 illustrates a distal portion of a catheter tube of the RICC in accordance with some embodiments.
Figure 4:
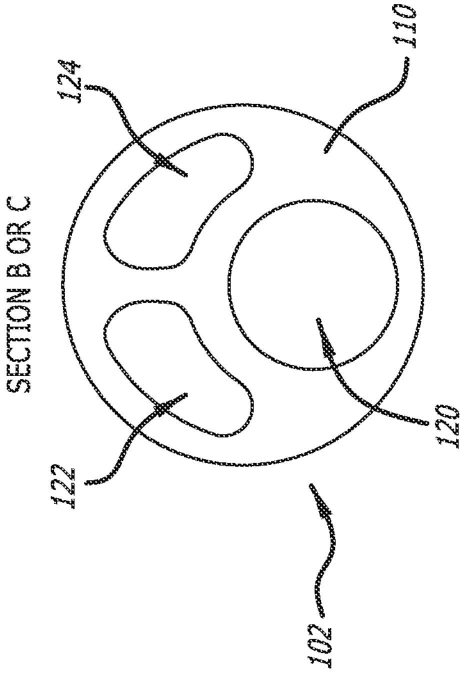
FIG. 4 illustrates a second transverse cross section of the distal portion of the catheter tube in accordance with some embodiments.
Figure 3:
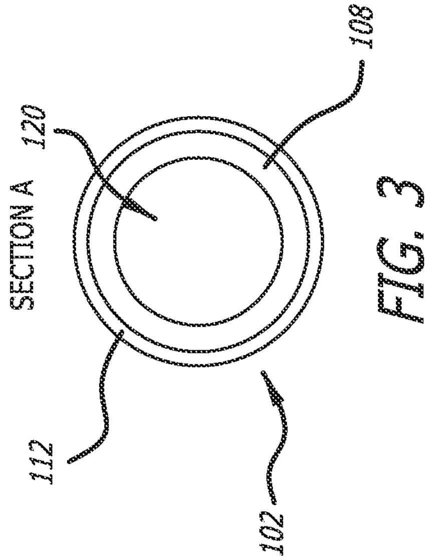
FIG. 3 illustrates a first transverse cross section of the distal portion of the catheter tube in accordance with some embodiments.
Figure 5:
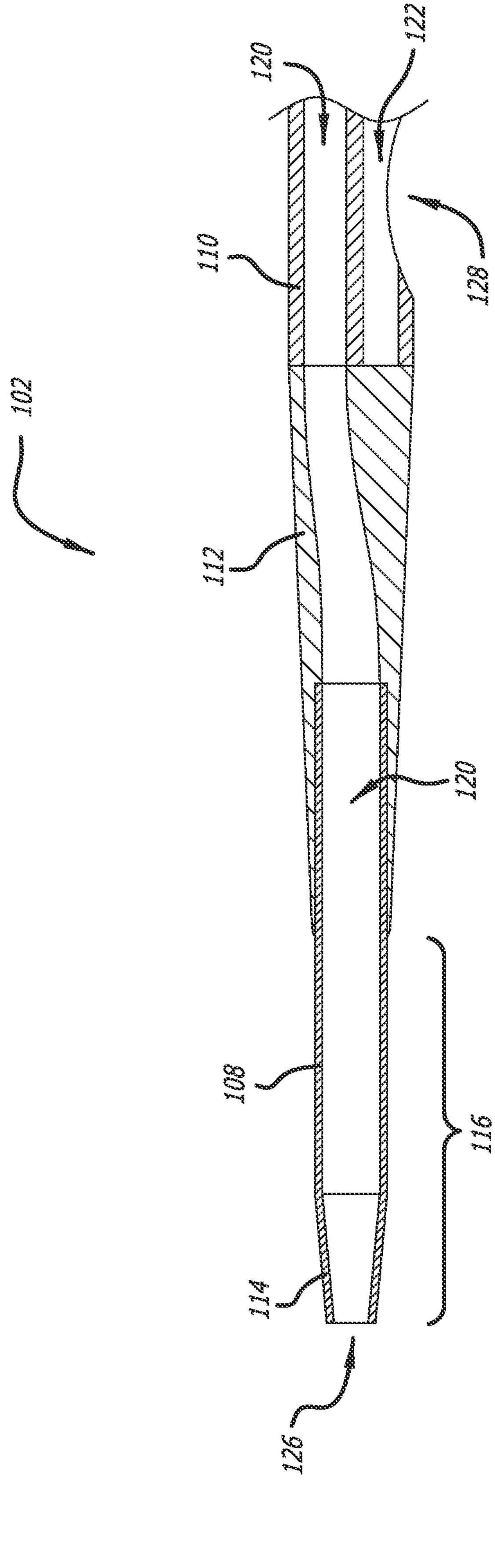
FIG. 5 illustrates a longitudinal cross section of the distal portion of the catheter tube in accordance with some embodiments.
Figure 6:
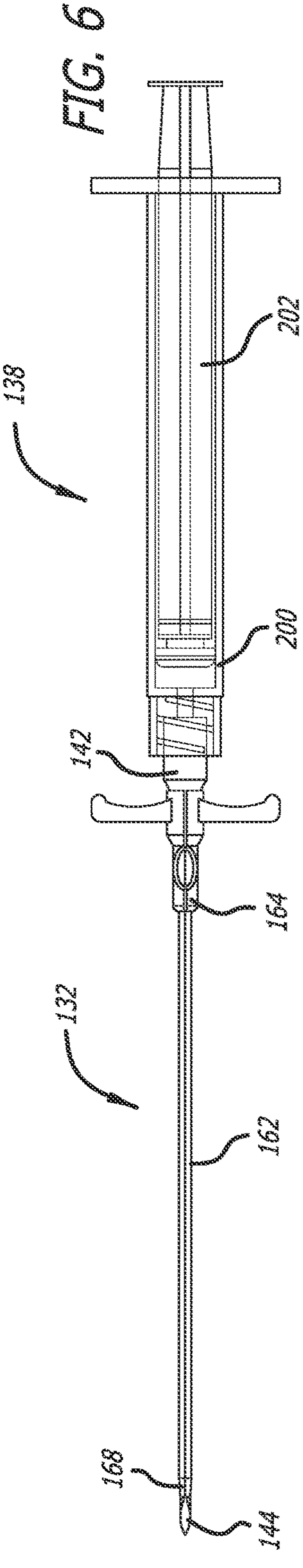
FIG. 6 illustrates a first view of an introducer with a syringe for inserting the RICC in a patient in accordance with some embodiments.
Figure 7:
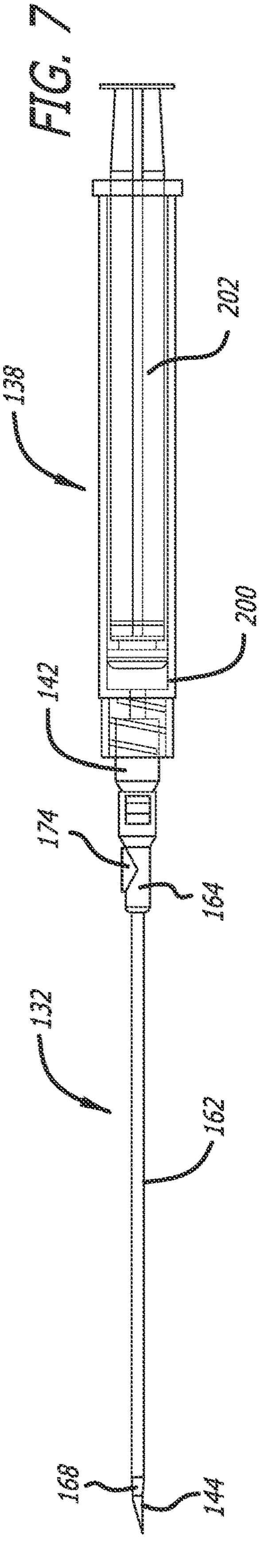
FIG. 7 illustrates a second view of the introducer with the syringe in accordance with some embodiments.
Figure 8:
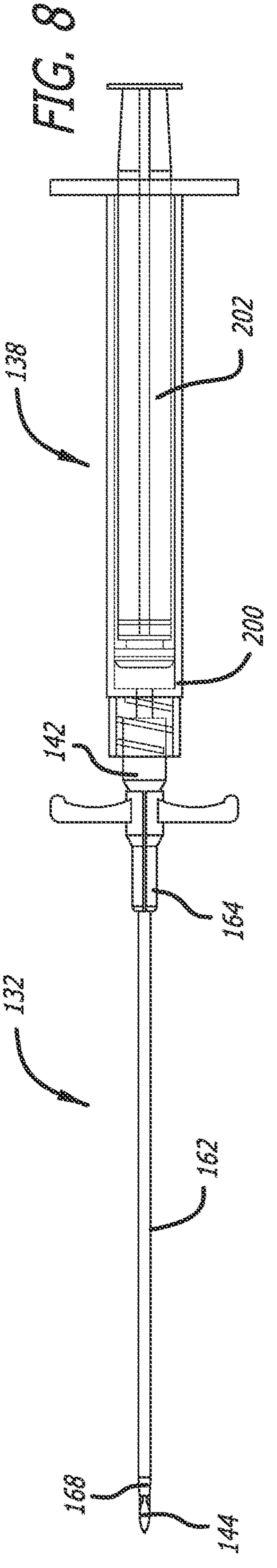
FIG. 8 illustrates a third view of the introducer with the syringe in accordance with some embodiments.

FIG. 1 illustrates a RICC 100 in accordance with some embodiments. FIG. 2 illustrates a distal portion of a catheter tube 102 of the RICC 100 in accordance with some embodiments. FIGS. 3-5 illustrate different cross section of the distal portion of the catheter tube 102 in accordance with some embodiments.

As shown, the RICC 100 includes the catheter tube 102, a catheter hub 104, and one or more extension legs 106.

The catheter tube 102 includes a first section 108 in the distal portion of the catheter tube 102, a second section 110 in the distal portion of the catheter tube 102 proximal of the first section 108, and a tapered junction 112 between the first and second sections 108 and 110 of the catheter tube 102.

The first section 108 of the catheter tube 102 includes a distal tip 114 having a relatively short taper from an outer diameter of a distal end of the first section 108 to an outer diameter of a remainder of the first section 108. The taper of the distal tip 114 is configured for immediate dilation of tissue about a needle tract established with the introducer 132 or 184 up to the outer diameter of the remainder of the first section 108 of the catheter tube 102. As best shown in FIG. 5, the first section 108 of the catheter tube 102 also includes a proximal portion disposed in a bore of a distal portion of the junction 112 and fixedly coupled thereto such as by a solvent bond, an adhesive bond, or a heat weld.

The second section 110 of the catheter tube 102 includes a consistent outer diameter over its length from a distal end of the second section 110 to a proximal end of the second section 110. The consistent diameter of the second section 110 of the catheter tube 102 is configured for smooth insertion into the needle tract and targeted vasculature subsequent to any dilation by the first section 108 of the catheter tube 102 and the junction 112. The distal end of the second section 110 of the catheter has a flat face flush with a flat-faced proximal end of the junction 112 and fixedly coupled thereto such as by a solvent bond, an adhesive bond, or a heat weld.

The junction 112 includes a taper over its length from a distal end of the junction 112 to the proximal end of the junction 112. The taper of the junction 112 is configured for immediate dilation of the tissue about the needle tract from the outer diameter of a majority of the first section 108 of the catheter tube 102 to the outer diameter of the second section 110 of the catheter tube 102. An abluminal surface of the junction 112 smoothly transitions from an abluminal surface of the first section 108 of the catheter tube 102 to an abluminal surface of the second section 110 of the catheter tube 102 without edges that catch on skin when the catheter tube 102 is inserted into the needle tract. In addition to the edges being minimal to negligible, the edges can include solvent-interdiffused polymeric material of the polymeric materials from which the catheter tube 102 is formed, which smoothens the transitions from the first section 108 of the catheter tube 102 to the junction 112 and from the junction 112 to the second section 110 of the catheter tube 102. Notably, the junction 112 has a length approximately commensurate with a length of an exposed portion 116 of the first section 108 of the catheter tube 102 or between lengths of exposed portions of the first and second sections 108 and 110 of the catheter tube 102. As such, the length of the exposed portion 116 of the first section 108 of the catheter tube 102 is less than the length of the junction 112 up to approximately commensurate with the length of the junction 112.

The first section 108 of the catheter tube 102 is formed of a first polymeric material (e.g., a polytetrafluoroethylene, a polypropylene, or a polyurethane) having a first durometer. The second section 110 of the catheter tube 102 is formed of a second polymeric material (e.g., a polyvinyl chloride, a polyethylene, another polyurethane, or a silicone) having a second durometer less than the first durometer. For example, the first section 108 of the catheter tube 102 can be formed of a first polyurethane having the first durometer while the second section 110 of the catheter tube 102 can be formed of a second, different polyurethane (e.g., a same or different diisocyanate or triisocyanate reacted with a different diol or triol, a different diisocyanate or triisocyanate reacted with a same or different diol or triol, etc.) having the second durometer less than the first durometer. Indeed, polyurethanes are advantageous for the catheter tube 102 in that polyurethanes can be relatively rigid at room-temperature but become more flexible in vivo at body temperature, which reduces irritation to vessel walls and phlebitis. Polyurethanes are also advantageous in that they can be less thrombogenic than some other polymers. The junction 112 is formed of the second polymeric material or a third polymeric material (e.g., yet another polyurethane) having a third durometer less than the first durometer and greater than, approximately equal to, or less than the second durometer.

It should be understood the first durometer of the first polymeric material, the second durometer of the second polymeric material, and the third durometer of the third polymeric material can be on different scales (e.g., Type A or Type D). With this understanding, the second durometer of the second polymeric material or the third durometer of the third polymeric material might not be numerically less than the first durometer of the first polymeric material when the second durometer or the third durometer is less than the first durometer. Indeed, the hardness of the second polymeric material or the third polymeric material can still be less than the hardness of the first polymeric material as the different scales—each of which ranges from 0 to 100—are designed for characterizing different materials in groups of the materials having a like hardness.

In accordance with the first section 108 of the catheter tube 102, the second section 110 of the catheter tube 102, and the junction 112 between the first and second sections 108 and 110 of the catheter tube 102 set forth above, the catheter tube 102 possesses a column strength sufficient to prevent buckling of the catheter tube 102 when inserted into a needle tract established by a percutaneous puncture with the introducer 132 or 184 set forth below. The column strength of the catheter tube 102 is also sufficient to prevent buckling of the catheter tube 102 when advanced through a vasculature of a patient without dilation of tissue about the needle tract or any blood vessels of the vasculature beforehand with a separate dilator.

The catheter tube 102 includes one or more catheter-tube lumens extending through the catheter tube 102; however, only one catheter-tube lumen typically extends from a proximal end of the catheter tube 102 to a distal end of the catheter tube 102 in a multiluminal RICC (e.g., a diluminal RICC, a triluminal RICC, a tetraluminal RICC, a pentaluminal RICC, a hexaluminal RICC, etc.). (See FIGS. 3-5.) Indeed, the first section 108 of the catheter tube 102 typically includes a single lumen therethrough as shown in FIG. 5.

The catheter hub 104 is coupled to a proximal portion of the catheter tube 102. The catheter hub 104 includes one or more catheter-hub lumens corresponding in number to the one-or-more catheter-tube lumens. The one-or-more catheter-hub lumens extends through an entirety of the catheter hub 104 from a proximal end of the catheter hub 104 to a distal end of the catheter hub 104.

Each extension leg of the one-or-more extension legs 106 is coupled to the catheter hub 104 by a distal portion thereof. The one-or-more extension legs 106 respectively include one or more extension-leg lumens, which, in turn, correspond in number to the one-or-more catheter-hub lumens. Each extension-leg lumen of the one-or-more extension-leg lumens extends through an entirety of the extension leg from a proximal end of the extension leg to a distal end of the extension leg.

Each extension leg of the one-or-more extension legs 106 includes a Luer connector 118 coupled to the extension leg, through which Luer connector 118 the extension leg and the extension-leg lumen thereof can be connected to another medical device and a lumen thereof.

As shown, the RICC 100 is a triluminal RICC including a set of three lumens; however, the RICC 100 is not limited to the set of the three lumens as set forth above. The set of three lumens includes a primary lumen 120, a secondary lumen 122, and a tertiary lumen 124 formed of fluidly connected portions of three catheter-tube lumens, three catheter-hub lumens, and three extension-leg lumens. The primary lumen 120 has a primary-lumen aperture 126 in the distal end of the first section 108 of the catheter tube 102, which corresponds to the distal end of the catheter tube 102 and a distal end of the RICC 100. The secondary lumen 122 has a secondary-lumen aperture 128 in a side of the distal portion of the catheter tube 102. The tertiary lumen 124 has a tertiary-lumen aperture 130 in the side of the distal portion of the catheter tube 102 proximal of the secondary-lumen aperture 128.

Introducers

Figure 9:
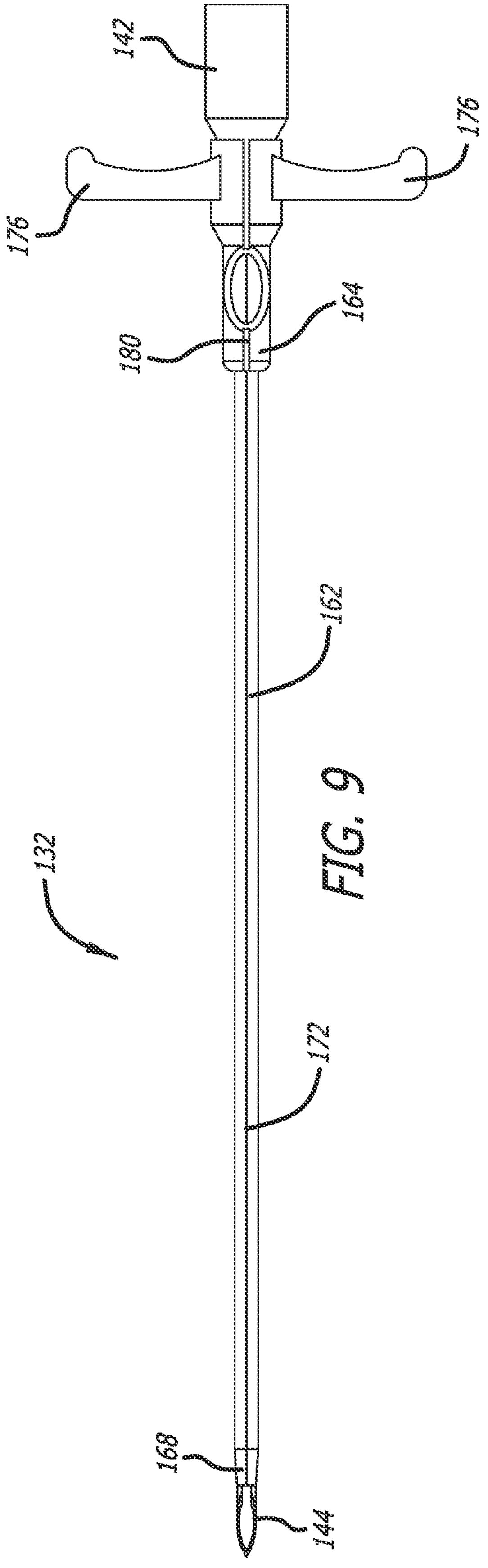
FIG. 9 illustrates a first view of the introducer without the syringe in accordance with some embodiments.
Figure 10:
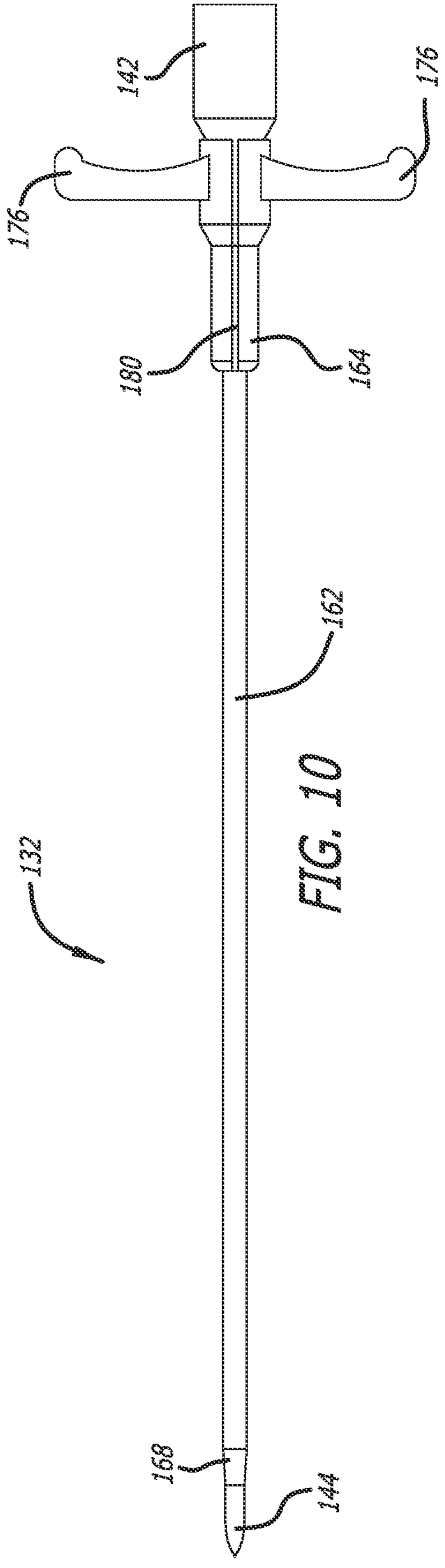
FIG. 10 illustrates a second view of the introducer without the syringe in accordance with some embodiments.
Figure 11:
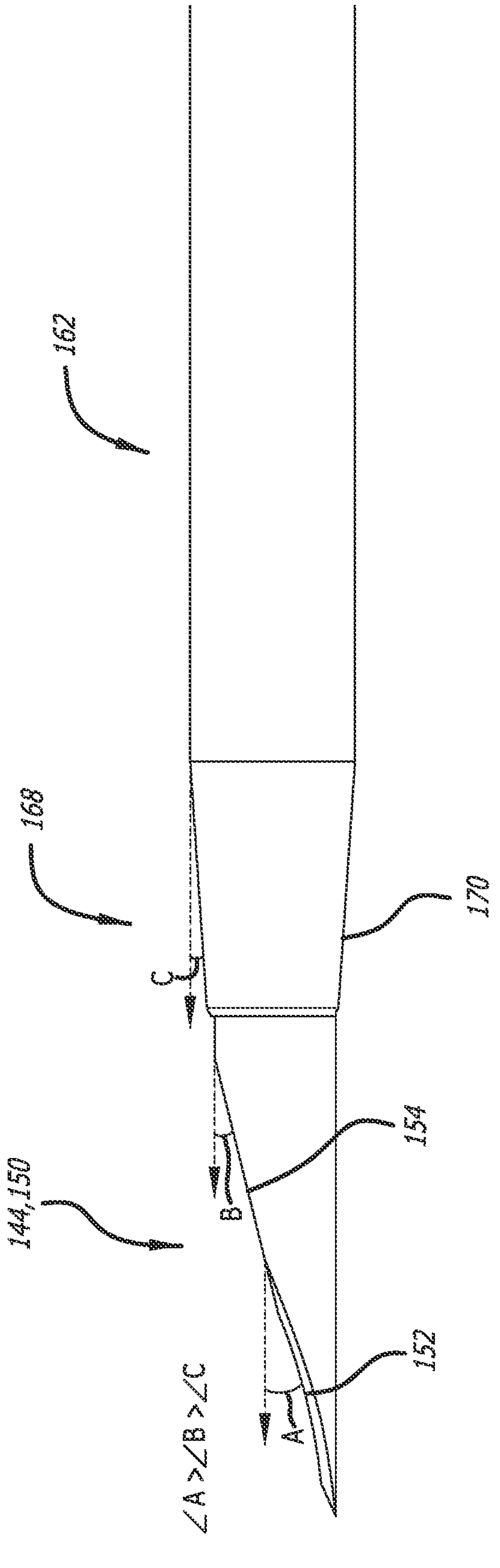
FIG. 11 illustrates a distal portion of the introducer in accordance with some embodiments.

FIGS. 6-10 illustrate different views of an introducer 132 including an introducer needle 134 and a splittable introducer sheath 136 with and without a syringe 138 in accordance with some embodiments. FIG. 11 illustrates a distal portion of the introducer 132 in accordance with some embodiments.

As shown, the introducer 132 includes the introducer needle 134 and the introducer sheath 136. In at least a ready-to-operate state of the introducer 132 configured for inserting the RICC 100 into a patient, the introducer needle 134 is disposed in the introducer sheath 136. Said differently, the introducer sheath 136 is disposed over the introducer needle 134 in at least the ready-to-operate state of the introducer 132, which is shown in FIGS. 6-10 and 15-17.

Figure 13:
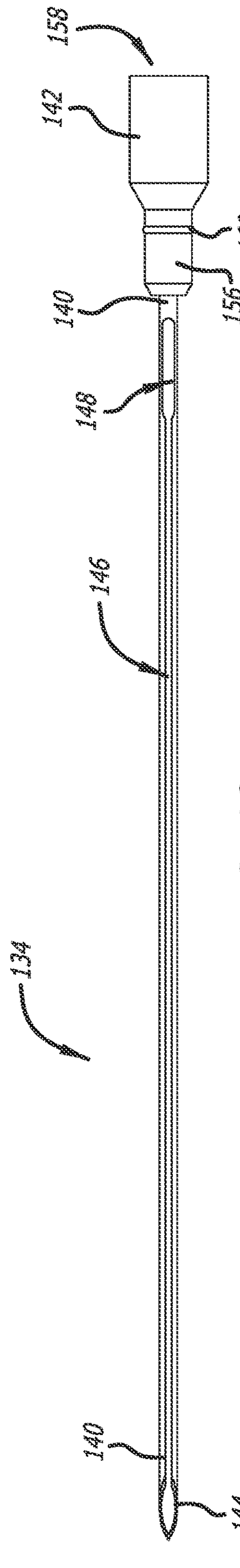
FIG. 13 illustrates an introducer needle of the introducer in accordance with some embodiments.

FIG. 13 illustrates the introducer needle 134 of the introducer 132 in accordance with some embodiments.

The introducer needle 134 includes a needle shaft 140 and a needle hub 142 coupled to a proximal portion of the needle shaft 140.

The needle shaft 140 includes a needle tip 144 in a distal portion of the needle shaft 140, a longitudinal gap 146, and a notch 148 in the proximal portion of the needle shaft 140 distal of the needle hub 142.

The needle tip 144 includes a bevel 150 having a tip bevel 152 and a primary bevel 154 proximal of the tip bevel 152. A tip-bevel angle (see ∠A in FIG. 11) of the tip bevel 152 is greater than a primary-bevel angle (see ∠B in FIG. 11) of the primary bevel 154 such that the bevel 150 provides a smooth transition over the needle tip 144. Such a needle tip is thusly configured for establishing a needle tract from an area of skin into a blood-vessel lumen of a patient in accordance with the needle tract-establishing step of the method set forth below.

The longitudinal gap 146 distally extends from the notch 148 in the needle shaft 140 through the needle tip 144, thereby forming a needle channel along a majority of a length of the introducer needle 134 as opposed to a needle lumen therethrough. (Notably, the introducer needle 134 includes a needle lumen; however, the needle lumen proximally extends from the notch 148 in the needle shaft 140 through a proximal end of the needle hub 142.) The longitudinal gap 146 has a width sized in accordance with an outer diameter of the access guidewire 208 set forth below, which allows the access guidewire 208 to pass from the wider notch 148 in the needle shaft 140 through the needle tip 144 when the introducer needle-withdrawing step of the method set forth below is performed.

The needle hub 142 can include a tapered or non-tapered male needle-hub connector 156 in a distal portion of the needle hub 142 and a tapered female needle-hub connector 158 in a proximal portion of the needle hub 142. The male needle-hub connector 156 is configured to form a fluid-tight connection with the female sheath-hub connector 182 set forth below in at least the ready-to-operate state of the introducer 132. When the male needle-hub connector 156 is not tapered, the male needle-hub connector 156 includes an 'O'-ring 160 disposed in a circumferential groove around the male needle-hub connector 156 configured to form the fluid-tight connection. Such a 'O'-ring is not needed when the male needle-hub connector 156 is not tapered. The female needle-hub connector 158 is configured to form a fluid-tight connection with the syringe tip 204 of the syringe 138 set forth below.

Figure 14:
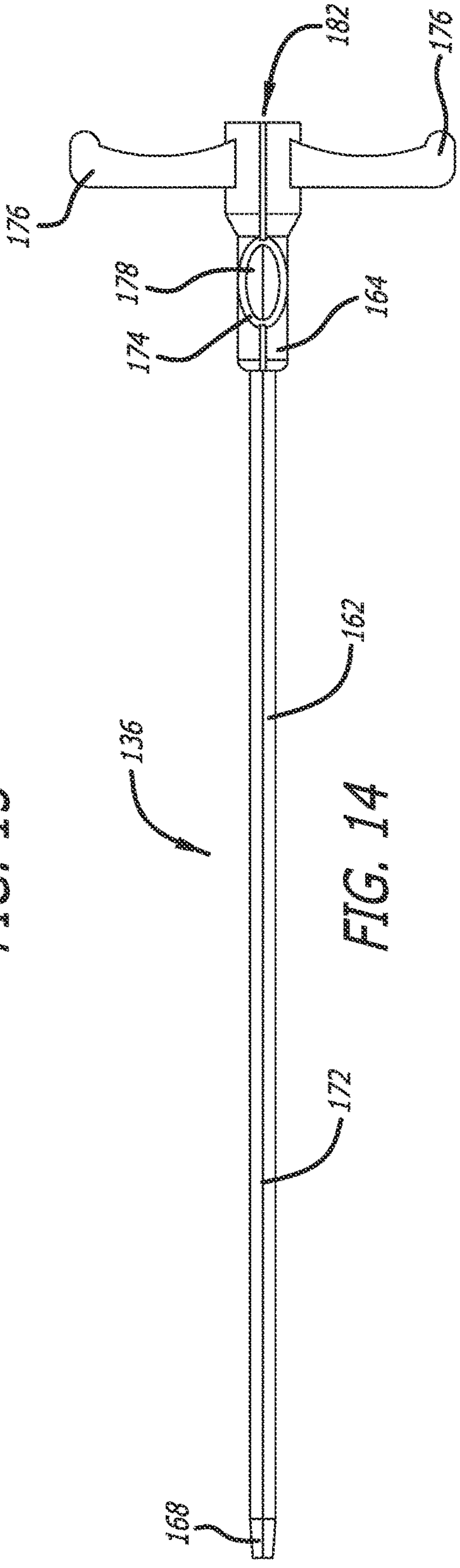
FIG. 14 illustrates a splittable introducer sheath of the introducer in accordance with some embodiments.

FIG. 14 illustrates the introducer sheath 136 of the introducer 132 in accordance with some embodiments.

The introducer sheath 136 includes a splittable sheath body 162 and a splittable sheath hub 164 coupled to a proximal portion of the sheath body 162. The introducer sheath 136 is configured such that an entirety of the introducer sheath 136 is disposed over the needle shaft 140 and needle hub 142 of the introducer needle 134 in at least the ready-to-operate state of the introducer 132.

The sheath body 162 includes an aperture 166 in the proximal portion of the sheath body 162 and a sheath tip 168 in a distal portion of the sheath body 162. (See FIG. 12 for the aperture 166.) Notwithstanding the aperture 166, which is covered by the sheath hub 164 coupled to the proximal portion of the sheath body 162, the sheath body 162 is configured to seal the needle shaft 140 such that a vacuum can be drawn through the introducer needle 134 in at least the ready-to-operate state of the introducer 132 shown in FIGS. 6-10 and 15-17.

The aperture 166 has a width approximately commensurate with a width of the notch 148 in the needle shaft 140, which is wider than the width of the longitudinal gap 146 of the needle shaft 140 sized in accordance with the diameter of the access guidewire 208. The aperture 166 is thusly configured to allow the access guidewire 208 to pass through the aperture 166 and into the notch 148 of the needle shaft 140 in at least the ready-to-operate state of the introducer 132.

The sheath tip 168 includes a taper 170 from an outer diameter of the needle shaft 140 up to an outer diameter of a majority of the sheath body 162. Said differently, the taper 170 is from the outer diameter of the majority of the sheath body 162 down to the outer diameter of the needle shaft 140. The taper 170 has a taper angle (see ∠C in FIG. 11) less than the primary-bevel angle (see ∠B in FIG. 11) of the primary bevel 154 of the needle tip 144, which, in turn, is less than the tip-bevel angle (see ∠A in FIG. 11) of the tip bevel 152 of the needle tip 144. The sheath tip 168 including such a taper is configured to provide a smooth transition from the needle tip 144 to the sheath body 162 in the ready-to-operate state of the introducer 132.

Figure 12:
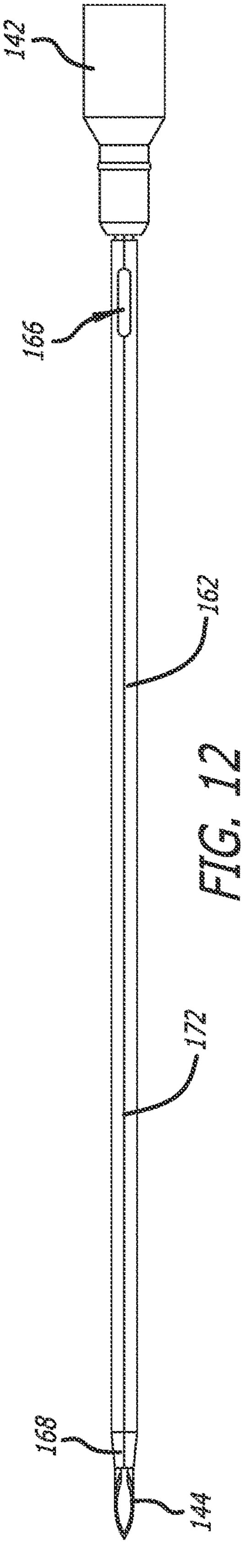
FIG. 12 illustrates the introducer without a sheath hub for description only.

The sheath body 162 can also include one or more longitudinal body faults 172 (e.g., grooves, lines of weakened material, etc.) such as a pair of the body faults 172 extending along opposing sides of the sheath body 162 if the sheath body 162 is not formed of a material configured to split or propagate one or more splits. For example, the sheath body 162 can be formed of a polymeric material such as polytetrafluoroethylene, which facilitates smooth, consistent splitting of the sheath body 162 without the body faults 172 along the sides of the sheath body 162. Indeed, such a sheath body can be configured to split against the access guidewire 208 set forth below when the sheath body 162 is pulled away from the access guidewire 208 after splitting the sheath hub 164. When present, the one-or-more body faults 172 include at least a primary body fault extending along at least a portion of a primary side of the introducer sheath 136 including the port 174. Indeed, the primary body fault can extend along an entirety of the sheath body 162 as shown in FIG. 12. When the pair of the body faults 172 is present, a secondary body fault extends along at least a portion of a secondary side of the introducer sheath 136 opposite the primary side. While not shown, the secondary body fault can also extend along the entirety of the sheath body 162.

The sheath hub 164 includes a splittable valved port 174 in the primary side of the introducer sheath 136 and a pair of tabs 176 extending from the sheath hub 164 proximal of the port 174.

Figure 16:
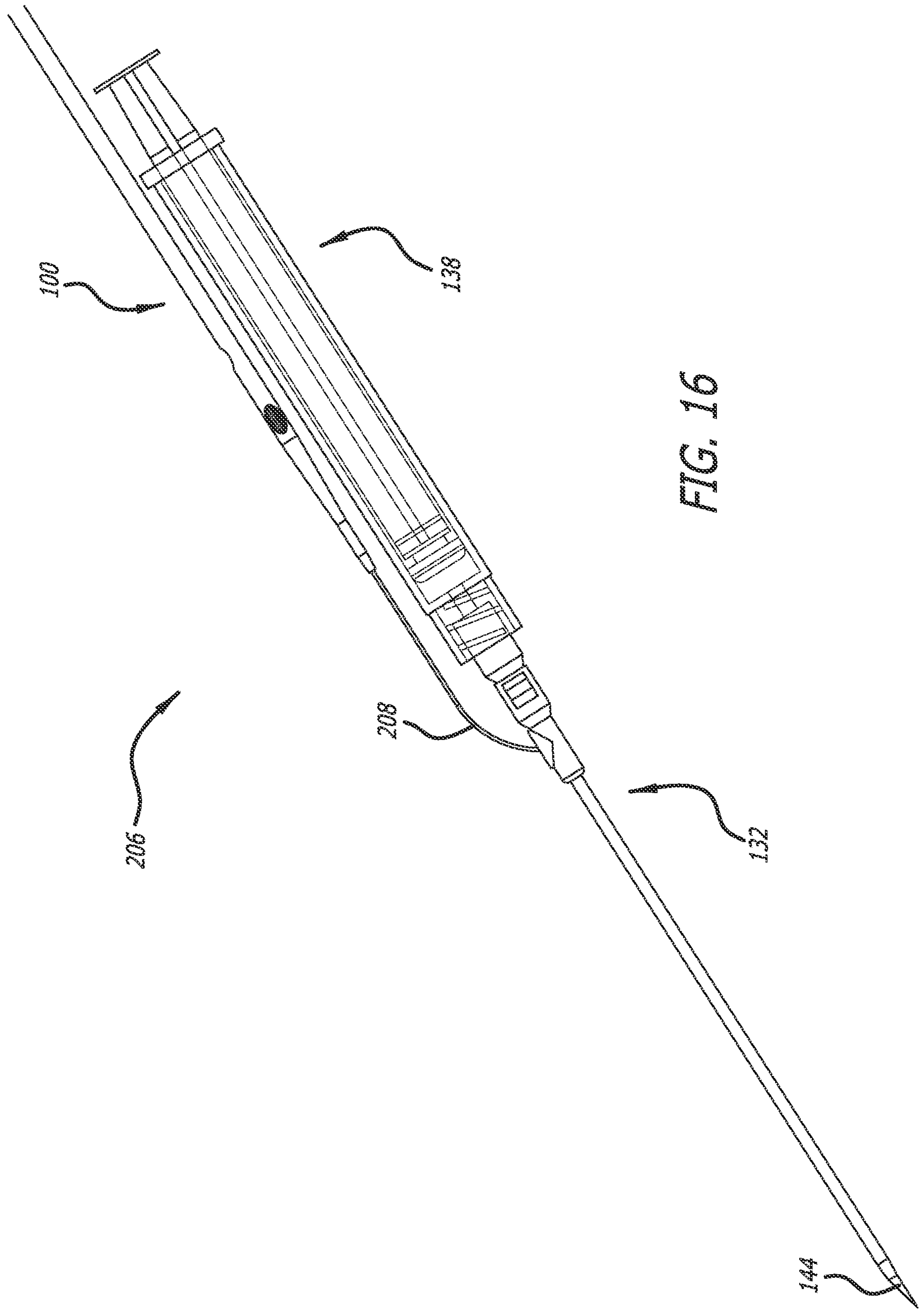
FIG. 16 illustrates a first view of a distal portion of the RICC insertion assembly in accordance with some embodiments.
Figure 17:
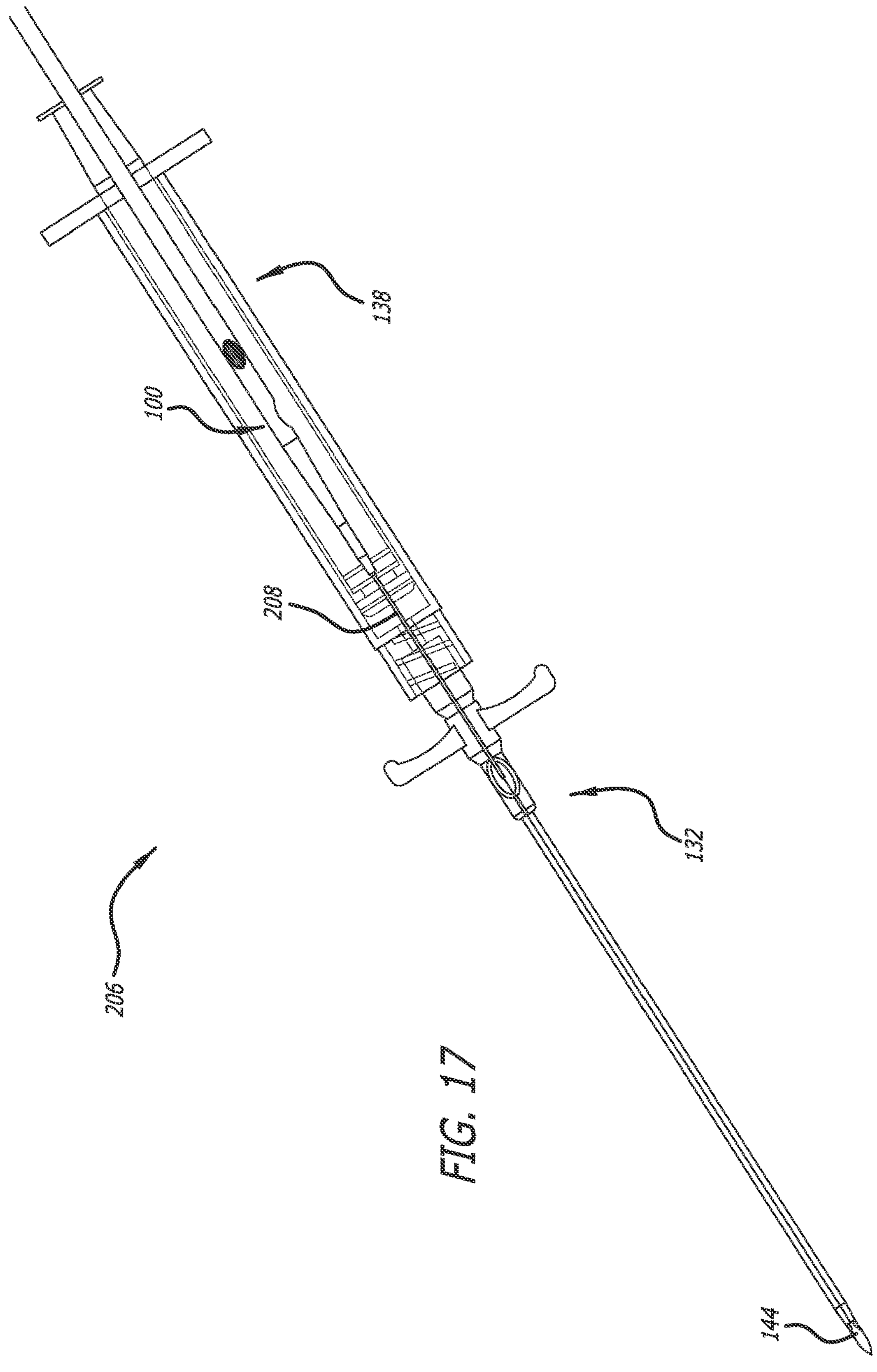
FIG. 17 illustrates a second view of the distal portion of the RICC insertion assembly in accordance with some embodiments.

The port 174 lies over the aperture 166 in the proximal portion of the sheath body 162. While the port 174 has a length approximately commensurate with a length of the aperture 166, a width of the port 174 is wider than the width of the aperture 166 to accommodate a valve 178 such as a tearable septum, a partially split septum, or a fully split septum compressed in the port 174 over the aperture 166 of the sheath body 162. As best shown in FIGS. 16 and 17, the valve 178 is configured to allow the access guidewire 208 to pass through the valve 178, through the port 174, and into the aperture 166 of the sheath body 162, notably, while maintaining fluid-tight access to a blood-vessel lumen of a patient with the introducer 132 and, thereby, enabling the blood-aspirating step of the method set forth below. Such a valve is also configured to split with a remainder of the sheath hub 164 for splitting the introducer sheath 136 away from the access guidewire 208 in accordance with the introducer sheath-splitting step of the method set forth below.

The tabs 176 radially extend from opposing sides of the sheath hub 164 orthogonal to the primary and secondary sides of the introducer sheath 136, which, in turn, positions the tabs 176 orthogonal to at least the primary fault when present in the primary side of the introducer sheath 136. Such tabs are configured to split the sheath hub 164 when the tabs 176 are pulled apart from each other in accordance with the introducer sheath-splitting step of the method set forth below. Notwithstanding the foregoing, the tabs 176 need not be 180° apart from each other as shown. Indeed, the tabs 176 can radially extend from sides of the sheath hub 164 that are less than 180° apart, including less than 135° apart, such as less than 90° apart, for example, about 67.5° apart, with the port 174 opposite a vertex of an internal angle formed between the tabs 176. Such tabs are configured to split the sheath hub 164 when the tabs 176 are pushed into each other such as by pinching the tabs 176 together with a single hand.

The sheath hub 164 can also include a pair of longitudinal hub faults 180 (e.g., grooves, lines of weakened material, etc.) extending along opposing sides of the sheath hub 164. When present, the hub faults 180 include a primary hub fault and a secondary hub fault. The primary hub fault extends along at least a portion of the primary side of the introducer sheath 136 (i.e., the side of the introducer sheath 136 including the port 174). Indeed, the primary hub fault can extend along an entirety of the sheath hub 164 as shown in FIG. 9. Likewise, the secondary hub fault extends along at least a portion of the secondary side of the introducer sheath 136 opposite the primary side. As shown in FIG. 10, the secondary hub fault can also extend along the entirety of the sheath hub 164. The sheath hub 164 is configured to split along both the primary and secondary hub faults 180 when the tabs 176 are pulled apart (or pinched together) for propagating one or more splits resulting from splitting the sheath hub 164 along the sheath body 162 in the primary and secondary sides of the introducer sheath 136.

The sheath hub 164 can also include a tapered or non-tapered female sheath-hub connector 182 in a proximal portion of the sheath hub 164. The female sheath-hub connector 182 is configured to form a fluid-tight connection with the male needle-hub connector 156 set forth above in at least the ready-to-operate state of the introducer 132. Notably, non-tapered connectors are less likely to get stuck together than tapered connectors (e.g., Luer-tapered connectors), which is advantageous for the introducer needle-withdrawing step of the method set forth below, as the introducer needle-withdrawing step includes withdrawing the introducer needle 134 from the introducer 132 and leaving the introducer sheath 136 in place in a blood-vessel lumen of a patient.

Figure 18:
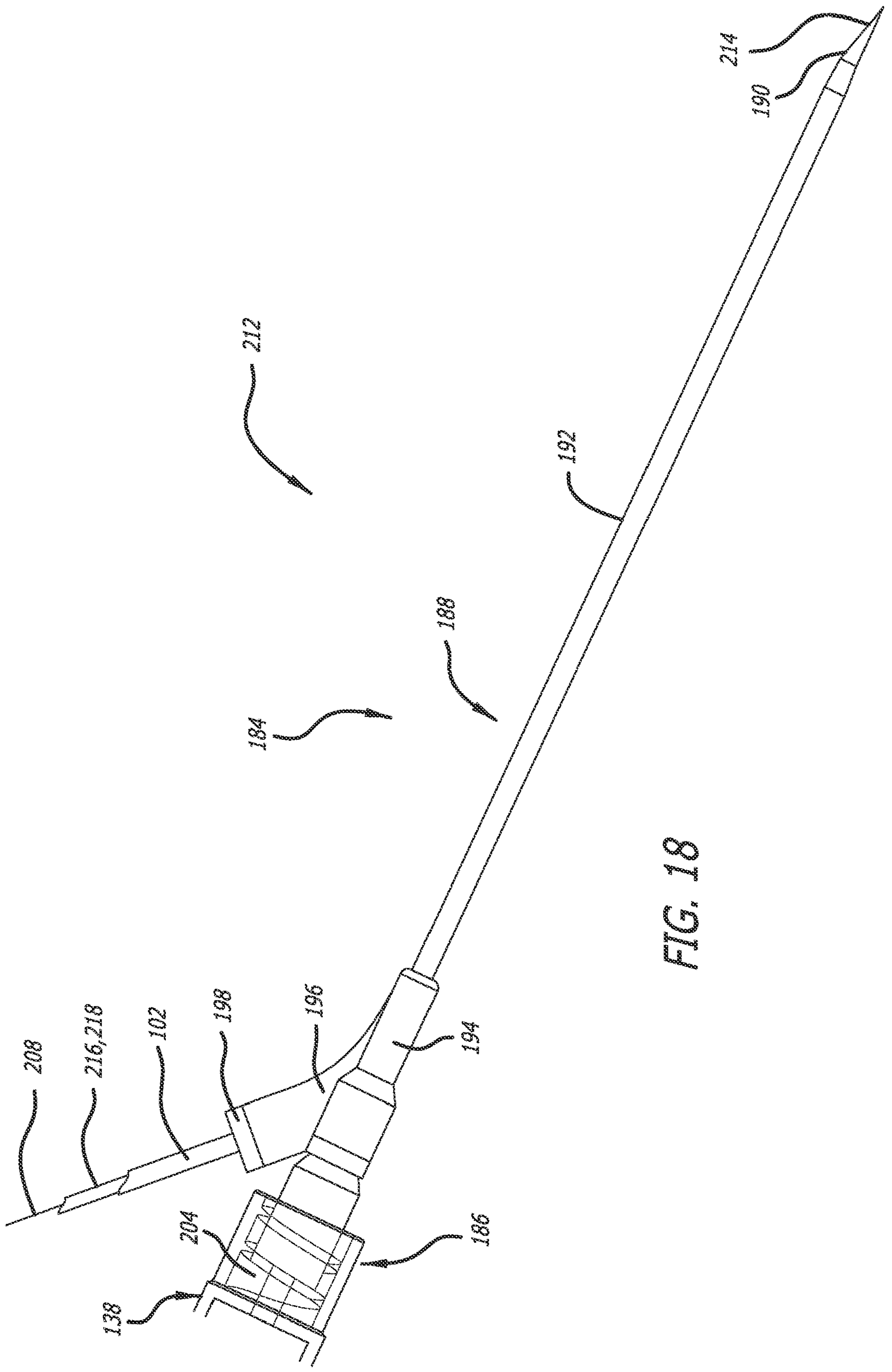
FIG. 18 illustrates a distal portion of another RICC insertion assembly in accordance with some embodiments.

FIG. 18 illustrates a distal portion of another introducer 184 in accordance with some embodiments.

Like the introducer 132, the introducer 184 includes an introducer needle 186 and a splittable introducer sheath 188.

The introducer needle 186 of the introducer 184 is similar to the introducer needle 134 of the introducer 132 set forth above except for one primary difference: 1) A needle shaft 190 of the introducer needle 186 is typically of a larger gauge (e.g., 18 gauge) than the needle shaft 140 of the introducer needle 134 for accepting the catheter tube 102 (e.g., 16 gauge) of the RICC 100 when inserted therein. As such, description for the introducer needle 134 of the introducer 132 set forth above is generally applicable to the introducer needle 186 of the introducer 184 except for the foregoing primary difference.

The introducer sheath 188 of the introducer 184 is similar to the introducer sheath 136 of the introducer 132 set forth above except for two primary differences: 1) A sheath body 192 of the introducer sheath 188 is typically of a larger gauge than the sheath body 162 of the introducer sheath 136 for accepting the needle shaft 190 of the introducer needle 186 when inserted therein. 2) A sheath hub 194 of the introducer sheath 188 includes a side arm 196 and a splittable valved port 198 in the side arm 196 of the sheath hub 194. In kind with the sheath body 192, the port 198 of the sheath hub 194 is typically larger than the port 174 of the sheath hub 164 for accepting the catheter tube 102 of the RICC 100 when inserted therein. Notably, when the primary and secondary hub faults are present, the hub faults extend along at least portions of the primary and secondary sides of the introducer sheath 188, respectively, wherein the primary side of the introducer sheath 188 includes the port 198. As such, description for the introducer sheath 136 of the introducer 132 set forth above is generally applicable to the introducer sheath 188 of the introducer 184 except for the foregoing two primary differences.

Whether the introducer 132 or 184, the introducer 132 or 184 can further include the syringe 138. The syringe 138 includes a barrel 200, a plunger 202 disposed in the barrel 200, and a tapered male syringe tip 204 extending from a distal portion of the syringe 138. The syringe tip 204 is configured to insert into the female needle-hub connector 158 set forth above in at least the ready-to-operate state of the introducer 132. Likewise, the syringe tip 204 is configured to insert into the female needle-hub connector of the introducer 184 shown in FIG. 18. Indeed, such a syringe is useful for at least aspirating blood in accordance with the blood-aspirating step of the method set forth below.

RICC Insertion Assemblies

Figure 15:
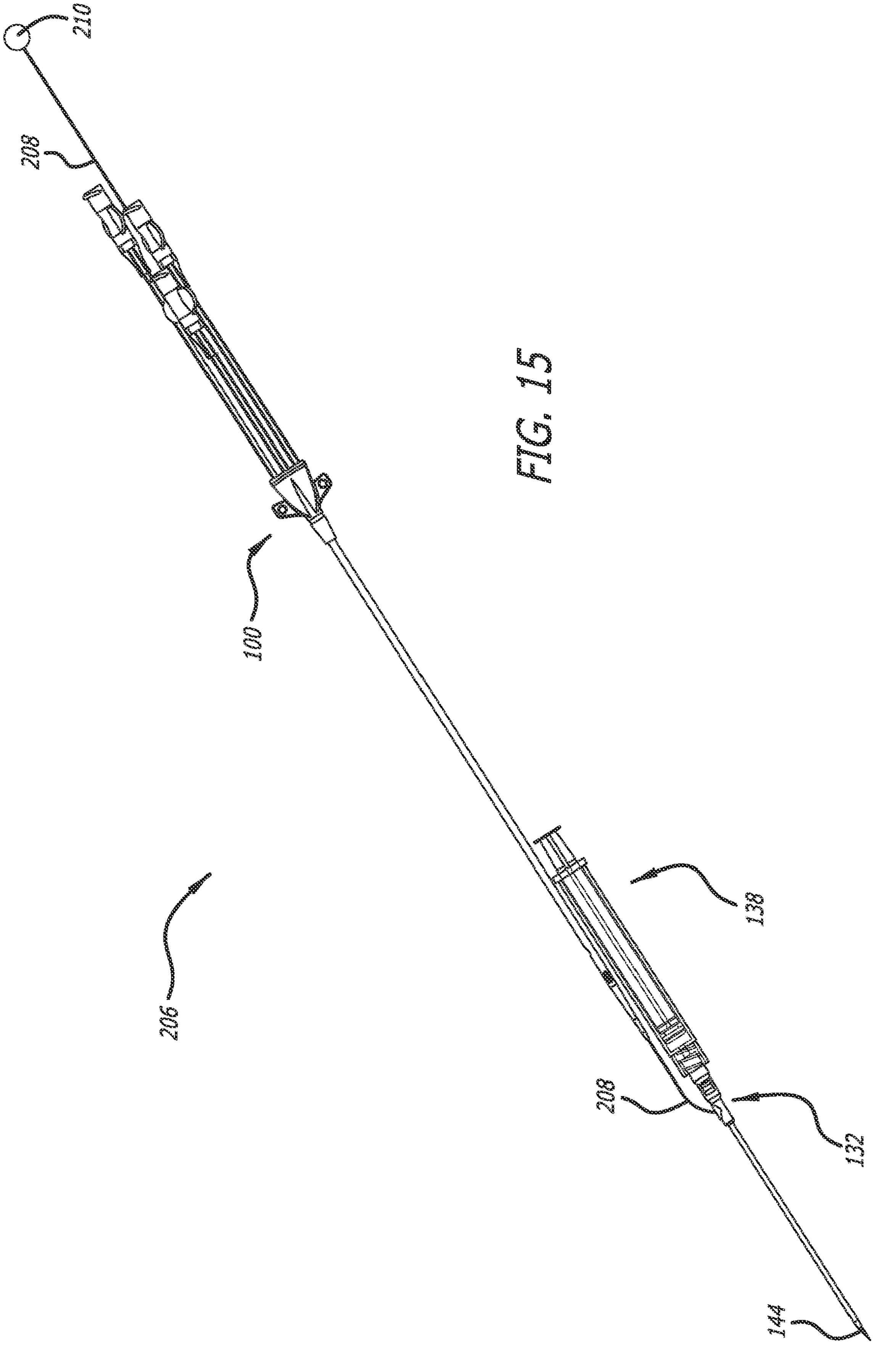
FIG. 15 illustrates a RICC insertion assembly in accordance with some embodiments.

FIGS. 15-17 illustrate different views of a RICC insertion assembly 206 in accordance with some embodiments.

As shown, the RICC insertion assembly 206 includes the RICC 100, the introducer 132, and an access guidewire 208 disposed in both the RICC 100 and the introducer 132 in at least a ready-to-operate state of the RICC insertion assembly 206.

Description for the RICC 100 and the introducer 132 is set forth above. Notably, in at least the ready-to-operate state of the RICC insertion assembly 206, the introducer 132 is also in its ready-to-operate state, description for which is also set forth above.

The access guidewire 208 extends along an entirety of the primary lumen 120 of the RICC 100, through the valve 178 (e.g., the septum) of the port 174 of the sheath hub 164 of the introducer sheath 136, along the sheath body-covered needle channel of the needle shaft 140 of the introducer needle 134, and to a location in the introducer 132 proximal of the needle tip 144. Notably, the access guidewire 208 includes a plain or non-wound portion as well as a wound portion less than about 7 cm, wherein the wound portion of the access guidewire 208 is in a distal portion of the access guidewire 208 including a distal end of the access guidewire 208. Because the valve 178 would leak if the wound portion of the access guidewire 208 extended therethrough, the plain or non-wound portion of the access guidewire 208 proximal of the wound portion extends through the valve 178. The location of the access guidewire 208 proximal of the needle tip 144 is advantageous for immediate advancement of the distal end of the access guidewire 208 through a remainder of the introducer 132 and into a blood-vessel lumen in accordance with the access guidewire-advancing step of the method set forth below following establishment of a needle tract to the blood vessel lumen. Notably, the access guidewire 208 also includes a stop 210 (e.g., a guidewire hub) about a proximal end of the access guidewire 208 configured to prevent over advancement of the access guidewire 208 during the access guidewire-advancing step and, thereby, loss of the access guidewire 208 within the RICC insertion assembly 206 or a patient, which can cause a guidewire embolism.

As set forth above for the introducer 132, the RICC insertion assembly 206 can further include the syringe 138 as shown. Again, such a syringe is useful for at least aspirating blood in accordance with the blood-aspirating step of the method set forth below.

FIG. 18 illustrates a distal portion of another RICC insertion assembly 212 in accordance with some embodiments.

Like the RICC insertion assembly 206, the RICC insertion assembly 212 includes the RICC 100, the introducer 184, and the access guidewire 208 in at least a ready-to-operate state of the RICC insertion assembly 212. Different than the RICC insertion assembly 206, however, the catheter tube 102 of the RICC 100 is disposed in the introducer 184 in at least the ready-to-operate state of the RICC insertion assembly 212. Indeed, the catheter tube 102 extends through the port 198 of the sheath hub 194 of the introducer sheath 188, along the side arm 196 of the sheath hub 194, along the sheath body-covered needle channel of the needle shaft 190 of the introducer needle 186, and to a location in the introducer 184 proximal of a needle tip 214 of the needle shaft 190. In addition, the RICC insertion assembly 212 can include a hollow stylet 216 disposed in the primary lumen 120 of the RICC 100 in at least the ready-to-operate state of the RICC insertion assembly 212, wherein a distal end of the stylet 216 extends to a same or different location proximal of the distal end of the catheter tube 102 in the introducer 184. Notably, the stylet 216 can be disposed in a Tuohy-Borst Luer connector (not shown) configured to couple to the extension leg including the extension leg-lumen portion of the primary lumen 120 of the RICC 100 and fluidly seal the primary lumen 120 with the stylet 216 therein. In combination with the port 198 of the sheath hub 194 for sealing the catheter tube 102 of the RICC 100 in the introducer sheath 188, the Tuohy-Borst Luer connector for sealing the stylet 216 in the primary lumen 120 of the RICC 100 and the sealing means for sealing the access guidewire 208 in the stylet lumen of the stylet 216 set forth below provide fluid-tight access to a blood-vessel lumen of a patient with the introducer 184, thereby enabling the blood-aspirating step of the method set forth below.

Description for the RICC 100, the introducer 184, and the access guidewire 208 is set forth above. Notably, in at least the ready-to-operate state of the RICC insertion assembly 212, the introducer 184 is also in its ready-to-operate state, description for which is also set forth above.

The stylet 216 includes a tubular stylet body 218 with a stylet lumen and a sealing means for sealing the stylet 216 selected from a sealable stylet hub (not shown) about a proximal portion of the stylet body 218 and one-or-more internal 'O'-rings.

The stylet body 218 is configured to occupy excess lumenal space in at least the ready-to-operate state of the RICC insertion assembly 212 between the access guidewire 208 disposed in the stylet 216 and a lumenal wall of the primary lumen 120 of the RICC 100. The stylet 216 is also configured to provide a structural support for advancing the access guidewire 208 within the RICC insertion assembly 212 in accordance with the access guidewire-advancing step of the method set forth below. Indeed, the stylet 216 reduces non-lumenal movement (i.e., movement not along or in line with a lumen) of the access guidewire 208 during the access guidewire-advancing step, which non-lumenal movement can damage the primary lumen 120 of the RICC 100 when the stylet 216 is absent. As such, the distal end of the access guidewire 208 should extend to a same or different location proximal of the distal end of the stylet 216 in at least the ready-to-operate state of the RICC insertion assembly 212 to obviate inadvertent non-lumenal movement. Again, the location of the access guidewire 208 proximal of the needle tip 214 is advantageous for immediate advancement of the distal end of the access guidewire 208 through a remainder of the introducer 184 and into a blood-vessel lumen in accordance with the access guidewire-advancing step following establishment of a needle tract to the blood vessel lumen.

When the sealing means for sealing the stylet 216 is the stylet hub, the stylet hub can include a Tuohy-Borst connector or a Luer connector configured to couple with another Tuohy-Borst Luer connector (i.e., a Tuohy-Borst Luer connector in addition to that set forth above for coupling to the extension leg of the RICC 100). The access guidewire 208 can be disposed in either the Tuohy-Borst connector or the other Tuohy-Borst Luer connector to fluidly seal the stylet lumen with the access guidewire 208 therein. (Notably, the stylet 216 can include the stylet hub optionally configured as the Luer connector when the sealing means for sealing the stylet 216 is the one-or-more internal 'O'-rings as the stylet hub is also configured to prevent any over advancement of the stylet 216.) When the sealing means for sealing the stylet 216 is the one-or-more internal 'O'-rings, the one-or-more internal 'O'-rings can be disposed in the stylet lumen in a proximal portion of the stylet 216, a distal portion of the stylet 216, or, for any two or more of the internal 'O'-rings, distributed between the proximal and distal portions of the stylet 216. The one-or-more internal 'O'-rings are configured to form a seal around the access guidewire 208 when the access guidewire 208 is disposed in the stylet 216. In combination with the port 198 of the sheath hub 194 for sealing the catheter tube 102 of the RICC 100 in the introducer sheath 188, the Tuohy-Borst Luer connector for sealing the stylet 216 in the primary lumen 120 of the RICC 100 and the sealing means for sealing the access guidewire 208 in the stylet lumen of the stylet 216 provide fluid-tight access to a blood-vessel lumen of a patient with the introducer 184, thereby enabling the blood-aspirating step of the method set forth below.

As set forth above for the introducer 132, the RICC insertion assembly 212 can further include the syringe 138 as shown. Again, such a syringe is useful for at least aspirating blood in accordance with the blood-aspirating step of the method set forth below.

RICC Insertion Kits

While not shown, a RICC insertion kit includes the RICC 100, the introducer 132 or 184, and the access guidewire 208, instructions for use of the RICC insertion kit, and packaging. If the RICC insertion kit includes the introducer 184, the RICC insertion kit further includes the stylet 216. The foregoing components of the RICC insertion assembly 206 or 212 are optionally assembled into a substantially ready-to-operate state of the RICC insertion assembly 206 or 212 in the RICC insertion kit and disposed in the packaging thereof. The instructions for use of the RICC insertion kit are either disposed in the packaging or printed on the packaging.

METHODS

A method of the RICC insertion assembly 206 or the components thereof includes a method for inserting the RICC 100 into a blood-vessel lumen of a patient. The method includes one or more steps selected from an assembly-acquiring step, a needle tract-establishing step, an introducer sheath-advancing step, an access guidewire-advancing step, an ultrasound-confirming step, a blood-aspirating step, an introducer needle-withdrawing step, an introducer sheath-splitting step, a RICC-advancing step, an access guidewire-withdrawing step, a maneuver guidewire-advancing step, an additional RICC-advancing step, and a maneuver guidewire-withdrawing step.

The assembly-acquiring step includes acquiring the RICC insertion assembly 206. Optionally, the RICC 100, the introducer 132, and the access guidewire 208 are directly acquired in a substantially ready-to-operate state of the RICC insertion assembly 206. If the RICC 100, the introducer 132, and the access guidewire 208 are not directly acquired in the substantially ready-to-operate state of the RICC insertion assembly 206, the assembly-acquiring step can include assembling the foregoing components to acquire the RICC insertion assembly 206 in at least the substantially ready-to-operate state of the RICC insertion assembly 206.

The needle tract-establishing step includes establishing a needle tract from an area of skin to the blood-vessel lumen with the introducer 132. The needle tract-establishing step can include drawing a slight vacuum with the syringe 138 while establishing the needle tract such that blood flashes back into at least the introducer needle 134 upon establishing the needle tract. In accordance with drawing such a vacuum, the needle tract-establishing step can include ensuring blood flashes back along the longitudinal gap 146 of the introducer needle 134 if the sheath body 162 is formed of a clear polymeric material, into the needle hub 142 of the introducer needle 134 if the needle hub 142 is formed of a clear polymeric material, into the syringe tip 204, into the barrel 200 of the syringe 138, or a combination thereof, thereby confirming the needle tract extends into the blood-vessel lumen.

The introducer sheath-advancing step includes advancing the introducer sheath 136 over the introducer needle 134 into the blood-vessel lumen to secure blood-vessel access for the RICC-advancing step. When the introducer sheath-advancing step is performed to secure the blood-vessel access for the RICC-advancing step, the introducer sheath-advancing step is performed before the access guidewire-advancing step. However, the access guidewire-advancing step can be alternatively performed to secure the blood-vessel access for the RICC-advancing step. When the access guidewire-advancing step is performed to secure the blood-vessel access for the RICC-advancing step, the introducer sheath-advancing step need not be performed.

The access guidewire-advancing step includes advancing the distal end of the access guidewire 208 from its initial location in the introducer 132 proximal of the needle tip 144 of the introducer needle 134 into the blood-vessel lumen to secure or maintain the blood-vessel access for the RICC-advancing step. The remainder of the access guidewire 208 proximally extends along the sheath body-covered needle channel of the needle shaft 140 of the introducer needle 134, through the valve 178 of the port 174 in the side of the sheath hub 164 of the introducer sheath 136, along the entirety of the primary lumen 120 of the RICC 100, and out a proximal end of the RICC 100. Again, the access guidewire 208 includes the stop 210 (e.g., the guidewire hub) about the proximal end of the access guidewire 208 configured to prevent over advancement of the access guidewire 208 during the access guidewire-advancing step.

The ultrasound-confirming step includes confirming with ultrasound imaging the access guidewire 208 is in the blood-vessel lumen after the access guidewire-advancing step.

The blood-aspirating step includes aspirating blood with the syringe 138 coupled to the introducer needle 134 for confirmation the needle tract extends into the blood-vessel lumen before performing the introducer needle-withdrawing step. As set forth above, the width of the longitudinal gap 146 in the needle shaft 140 of the introducer needle 134 is sized in accordance with the outer diameter of the access guidewire 208. The needle shaft 140, in turn, has an inner diameter sized in accordance with the width of the longitudinal gap 146 in the needle shaft 140 such that the inner diameter of the needle shaft 140 is greater than the outer diameter of the access guidewire 208. This advantageously enables the blood-aspirating step to be performed after the access guidewire-advancing step while the access guidewire 208 secures or maintains the blood-vessel access for the RICC-advancing step.

The introducer needle-withdrawing step includes withdrawing the introducer needle 134 from the introducer 132 leaving both the introducer sheath 136 and the access guidewire 208 in place in the blood-vessel lumen. Again, the introducer needle 134 includes the longitudinal gap 146 extending from the proximal portion of the needle shaft 140 through the needle tip 144, thereby enabling the introducer needle-withdrawing step while the access guidewire 208 remains in place in the blood-vessel lumen.

The introducer sheath-splitting step includes splitting the sheath hub 164 including the port 174 in the side of the sheath hub 164 by pulling apart the tabs 176 extending from the sheath hub 164. The introducer sheath-splitting step also includes propagating one or more splits resulting from splitting the sheath hub 164 along the sheath body 162 of the introducer sheath 136. Propagating the one-or-more splits can include continuing to pull apart the tabs 176 after splitting the sheath hub 164 or pulling the sheath body 162 away from the access guidewire 208 such that the sheath body 162 splits against the access guidewire 208. In this way, the introducer sheath 136 is split away from the access guidewire 208 to remove split portions of the introducer sheath 136 from the blood-vessel lumen. To maintain the blood-vessel access with the access guidewire 208 for the RICC-advancing step, it is advantageous to hold the access guidewire 208 or press it against the patient while the introducer sheath-splitting step is performed.

The RICC-advancing step includes advancing the distal portion of the catheter tube 102 of the RICC 100 over the access guidewire 208 and into the blood-vessel lumen, thereby inserting the RICC 100 into the blood-vessel lumen.

The access guidewire-withdrawing step includes withdrawing the access guidewire 208 leaving the catheter tube 102 in place in the blood-vessel lumen. The access guidewire-withdrawing step also includes removing the access guidewire 208 from the primary lumen 120 of the RICC 100 so the maneuver guidewire-advancing step can be performed.

The maneuver guidewire-advancing step includes advancing a maneuver guidewire into the blood-vessel lumen by way of the primary lumen 120 of the RICC 100. In accordance with the maneuver guidewire-advancing step, a distal portion of the maneuver guidewire can be advanced to a lower ⅓ of an SVC of a heart of the patient.

The additional RICC-advancing step includes advancing the distal portion of the catheter tube 102 farther into the blood-vessel lumen over the maneuver guidewire to the lower ⅓ of the SVC of the patient.

The maneuver guidewire-withdrawing step includes withdrawing the maneuver guidewire leaving the catheter tube 102 in place in the lower ⅓ of the SVC.

A method of the RICC insertion assembly 212 or the components thereof also includes a method for inserting the RICC 100 into a blood-vessel lumen of a patient. The method likewise includes one or more steps selected from the assembly-acquiring step, the needle tract-establishing step, the introducer sheath-advancing step, the access guidewire-advancing step, the ultrasound-confirming step, the blood-aspirating step, the introducer needle-withdrawing step, the introducer sheath-splitting step, the RICC-advancing step, the access guidewire-withdrawing step, the maneuver guidewire-advancing step, the additional RICC-advancing step, and the maneuver guidewire-withdrawing step. However, the method or the foregoing steps thereof can be modified as needed in accordance with features of the RICC insertion assembly 212. For example, the RICC-advancing step can be performed before the introducer sheath-splitting step as the catheter tube 102 of the RICC 100 is disposed in the introducer sheath 188 throughout the method until the introducer sheath-splitting step is performed. In addition, the method additional steps to the foregoing steps can be performed as needed in accordance with features of the RICC insertion assembly 212. For example, the method can include a stylet-withdrawing step. That said, the access-guidewire removing step can be modified to include withdrawing the stylet 216 together with the access guidewire 208 during the access-guidewire removing step.

While some particular embodiments have been disclosed herein, and while the particular embodiments have been disclosed in some detail, it is not the intention for the particular embodiments to limit the scope of the concepts provided herein. Additional adaptations or modifications can appear to those of ordinary skill in the art, and, in broader aspects, these adaptations or modifications are encompassed as well. Accordingly, departures may be made from the particular embodiments disclosed herein without departing from the scope of the concepts provided herein.

What is claimed is:

1. A rapidly insertable central catheter ("RICC") insertion assembly, comprising:

a RICC;

an introducer including:

an introducer needle including:

a needle shaft including a longitudinal gap distally extending from a notch in a proximal portion of the needle shaft through a needle tip; and a splittable introducer sheath disposed over the needle shaft, the splittable introducer sheath including:

a splittable sheath body sealing the longitudinal gap of the needle shaft such that a vacuum can be drawn through the introducer needle, the splittable sheath body including a sheath aperture over the notch in the needle shaft;

a splittable sheath hub coupled to a proximal portion of the splittable sheath body; and a splittable valved port in a side of the splittable sheath hub over the sheath aperture; and an access guidewire disposed in both the RICC and the introducer, the access guidewire extending along an entirety of a primary lumen of the RICC, through a valve of the splittable valved port, through the sheath aperture, along a sheath body-covered needle channel of the needle shaft, and to a location in the introducer proximal of the needle tip.

2. The RICC insertion assembly of claim 1, wherein the splittable sheath hub includes a non-tapered female sheath-hub connector in a proximal portion of the sheath hub.

3. The RICC insertion assembly of claim 2, wherein a needle hub coupled to the proximal portion of the needle shaft includes a non-tapered male needle-hub connector in a distal portion of the needle hub configured to form a fluid-tight connection with the non-tapered female sheath-hub connector.

4. The RICC insertion assembly of claim 3, wherein the non-tapered male needle-hub connector includes an ‘O’-ring disposed in a circumferential groove around the non-tapered male needle-hub connector configured to form the fluid-tight connection.

5. The RICC insertion assembly of claim 3, further comprising a syringe including a tapered male syringe tip extending from a distal portion of the syringe, the tapered male syringe tip configured to insert into a tapered female needle-hub connector in the proximal portion of the needle hub.

6. The RICC insertion assembly of claim 1, the RICC comprising a catheter tube including:

a first section formed of a first polymeric material having a first durometer, the first section located in a distal portion of the catheter tube;

a second section formed of a second polymeric material having a second durometer less than the first durometer, the second section located in the distal portion of the catheter tube proximal of the first section of the catheter tube; and a tapered junction between the first section and the second section of the catheter tube, the tapered junction having a length between that of exposed portions of the first section and the second section of the catheter tube.

7. The RICC insertion assembly of claim 6, wherein the catheter tube possesses a column strength sufficient to prevent buckling of the catheter tube when inserted into a needle tract established by a percutaneous puncture with the introducer and advanced through a vasculature of a patient without dilation of tissue about the needle tract or any blood vessels of the vasculature beforehand with a separate dilator.

8. The RICC insertion assembly of claim 1, wherein the valve includes a tearable or split septum compressed in the splittable valved port, the access guidewire extending through the tearable or split septum.

9. The RICC insertion assembly of claim 8, wherein the tearable or split septum lies over the notch in the needle shaft.

10. The RICC insertion assembly of claim 1, wherein the access guidewire includes a non-wound portion and a wound portion, the non-wound portion of the access guidewire extending through the valve of the splittable valved port.

11. The RICC insertion assembly of claim 1, wherein the splittable sheath body is configured to split against the access guidewire when the splittable sheath body is pulled away from the access guidewire after splitting the splittable sheath hub.

* * * * *